(12) United States Patent
Yin et al.

(10) Patent No.: US 10,165,964 B2
(45) Date of Patent: Jan. 1, 2019

(54) SYSTEMS AND METHODS FOR QUANTIFYING REGIONAL FISSURE FEATURES

(71) Applicant: Vida Diagnostics, Inc., Coralville, IA (US)

(72) Inventors: Youbing Yin, Coralville, IA (US); Philippe Raffy, Edina, MN (US)

(73) Assignee: Vida Diagnostics, Inc., Coralville, IA (US)

(*) Notice: Subject to any disclaimer, the term of this patent is extended or adjusted under 35 U.S.C. 154(b) by 97 days.

(21) Appl. No.: 15/148,767

(22) Filed: May 6, 2016

(65) Prior Publication Data

US 2016/0328850 A1    Nov. 10, 2016

Related U.S. Application Data

(60) Provisional application No. 62/159,098, filed on May 8, 2015.

(51) Int. Cl.
*G06T 7/00* (2017.01)
*A61B 5/055* (2006.01)
(Continued)

(52) U.S. Cl.
CPC .............. *A61B 5/08* (2013.01); *A61B 5/055* (2013.01); *A61B 6/032* (2013.01); *A61B 6/037* (2013.01);
(Continued)

(58) Field of Classification Search
CPC ......... A61B 5/055; A61B 6/032; A61B 6/037; A61B 5/08; A61B 6/50; A61B 6/5217;
(Continued)

(56) References Cited

U.S. PATENT DOCUMENTS 9,076,201 B1    7/2015  Negahdar et al.
9,760,989 B2    9/2017  Yin et al.
(Continued)

FOREIGN PATENT DOCUMENTS

JP    2005028121 A    2/2005
WO    WO 2014042902 A1 *  3/2014  ........... G06T 7/0012

OTHER PUBLICATIONS

Wei et al. "Segmentation of Lung Lobes in Volumetric CT images for Surgical Planning of Treating Lung Cancer." 28th Annual International Conference of the IEEE Engineering in Medicine and Biology Society, Aug. 30, 2006, pp. 4869-4872.*
(Continued)

*Primary Examiner* — Jon Chang
(74) *Attorney, Agent, or Firm* — Fredrikson & Byron, P.A.

(57) ABSTRACT

Analysis of pulmonary scans representative of a patient's pulmonary structure can be used to classify a patient into one or more of a plurality of populations. The patient's scan can be mapped to a reference domain and analyzed to determine one or more fissure features associated with a plurality of regions in the reference domain. Comparison of the determined fissure features with a plurality of fissure atlases, each associated with different population, can be performed to classify the patient into one or more of the populations. Data from different fissure atlases can be compared to determine regions in the fissure atlases that distinguish one population from another. Such distinguishing regions can improve the ability to classify the patient while reducing errors based on false classifications.

24 Claims, 17 Drawing Sheets

(51) Int. Cl.
| | |
|---|---|
| A61B 5/08 | (2006.01) |
| A61B 6/03 | (2006.01) |
| A61B 6/00 | (2006.01) |
| G06F 19/00 | (2018.01) |
| G06K 9/62 | (2006.01) |
| A61B 5/00 | (2006.01) |

(52) U.S. Cl.
CPC .............. *A61B 6/50* (2013.01); *A61B 6/5217* (2013.01); *G06F 19/321* (2013.01); *G06K 9/6267* (2013.01); *G06T 7/0014* (2013.01); *A61B 5/004* (2013.01); *G06K 2209/05* (2013.01); *G06T 2207/10072* (2013.01); *G06T 2207/30061* (2013.01)

(58) Field of Classification Search
CPC ..... A61B 5/004; G06F 19/321; G06T 7/0014; G06T 2207/30061; G06T 2207/10072; G06K 9/6267; G06K 2209/05
See application file for complete search history.

(56) References Cited

U.S. PATENT DOCUMENTS

| | | | |
|---|---|---|---|
| 2005/0190189 | A1 | 9/2005 | Chefd'hotel et al. |
| 2006/0030958 | A1 | 2/2006 | Tschirren et al. |
| 2007/0092864 | A1 | 4/2007 | Reinhardt et al. |
| 2011/0243403 | A1 | 10/2011 | Mizuno |
| 2012/0249546 | A1 | 10/2012 | Tschirren et al. |
| 2014/0105472 | A1 | 4/2014 | Yin et al. |
| 2015/0294462 | A1* | 10/2015 | Yin ....................... G06T 7/0012 382/128 |

OTHER PUBLICATIONS

International Search Report for PCT/US2016/031306, dated Sep. 2, 2016, 16 pages.
Li Zhang et al., "Atlas-Driven Lung Lobe Segmentation in Volumetric X-Ray CT Images," IEEE Transactions on Medical Imaging, vol. 25, No. 1, Jan. 2006, 16 pages.
Rui Min et al.,"Multi-Atlas Based Representations for Alzheimer's Disease Diagnosis," Hum Brain Mapp. 35(10): Oct. 2014, 36 pages.
Keelin Murphy, "Toward automatic regional analysis of pulmonary function using inspiration and expiration thoracic CT," Med. Phys. 39(3), Mar. 2012, 14 pages.
Eva M. Van Rikxoort, et al., "A method for the automatic quantification of the completeness of pulmonary fissures: evaluation in a database of subjects with severe emphysema," European Radiology (2012) pp. 302-309.
Jiantao PU., et al., "Computerized assessment of pulmonary fissure integrity using high resolution CT.," Am. Assoc. Phys. Med. 37(9), (2010), pp. 4661-4672.
Tschirren, J., et al., "Intrathoracic airway trees: segmentation and airway morphology analysis from low-dose CT scans," IEEE Trans. Med. Imaging, Dec. 24, 2005, (12):16 pages.
Juerg Tschirren., et al., "Matching and Anatomical Labeling of Human Airway Tree," IEEE Trans. Med Imaging., vol. 24, No. 12., Dec. 2005, pp. 1540-1547.
Juerg Tschirren, "Segmentation, Anatomical Labeling, Branchpoint Matching, and Quantitative Analysis of Human Airway Trees in Volumetric CT Images," Ph.D. Thesis, The University of Iowa, 2003; 231 pages.
Kang Li, Efficient Optimal Net Surface Detection for Image Segmentation—from Theory to Practice, M.Sc. Thesis, The University of Iowa, 2003, 68 pages.
Alejandro F. Frangi, et al., "Multiscale Vessel Enhancement Filtering," MICCAI, Image Sciences Institute, 1998; 1496(3): pp. 130-137.
Menkes H., et al., "Collateral ventilation," Fed. Proc., Jan. 1979; 38(1):22-6; 1 page.

Rafael Wiemker, et al., "Unsupervised extraction of the pulmonary interlobar fissures from high resolution thoracic CT data," International Congress Series 1281 (2005) 1121-1126.
"COPD Essentials for Health Professionals," Retrieved from: https://www.nhlbi.nih.gov/health/educational/copd/campaign-materials/html/providercard.htm on Aug. 18, 2014, 2 pages.
Felix J.F. Herth, et al., "Endoscopic Lung Volume Reduction," Respiration, vol. 79, No. 1, 2010, 9 pages.
Charlie Strange, et al., "Design of the Endobronchial Valve for Emphysema Palliation Trial (VENT): a non-surgical-method of lung volume reduction," BMC Pulmonary Medicine, vol. 7, Jul. 3, 2007, 12 pages.
March Riquet, et al., "Lung cancer invading the fissure to the adjacent lobe: more a question of spreading mode than a staging problem," European Journal of Cardio-Thoracic Surgery, vol. 41, 2012, 5 pages.
Van Rikxoort, E.M., et al., "Automatic Segmentation of Pulmonary Segments from Volumetric Chest C T Scans," IEEE Transactions on Medical Imaging, vol. 28, No. 4, Apr. 2009, 2 pages.
PU, J. et al., "Pulmonary Lobe Segmentation in CT Examinations Using Implicit Surface Fitting," IEEE Transactions on Medical Imaging, vol. 28, No. 12, Dec. 2009, 28 pages, Abstract and author manuscript provided.
Ukil, S., et al., "Anatomy-Guided Lung Lobe Segmentation in X-Ray CT Images," IEEE Transactions on Medical Imaging, vol. 28, No. 2, Feb. 2009, 2 pages, Abstract only.
Jan-Martin Kuhnigk, et al., "Lung lobe segmentation by anatomy-guided 3D watershed transform," Proceedings of SPIE Medical Imaging, vol. 4, 2003, 9 pages.
Xiangrong Zhou, et al., "Automatic recognition of lung lobes and fissures from multi-slice CT images," Proceedings of SPIE Medical Imaging, vol. 5370, 2004, 5 pages.
Marc Noppen, "Collateral Ventilation in End-Stage Emphysema: A Blessing or a Curse for New Bronchoscopic Treatment Approaches (or Both)?" Respiration, vol. 74, No. 5, Jan. 2007, 3 pages.
Joseph R. Rodarte, et al., "Regional lung strain in dogs during deflation from total lung capacity," Journal of Applied Physiology, vol. 85, 1985, 9 pages.
Helgo Magnussen, et al., "Effect of fissure integrity on lung volume reduction using a polymer sealant* in advanced emphysema," Thorax, vol. 67, No. 4, 2012, 8 pages.
Frank C. Sciurba, et al., "A Randomized Study of Endobronchial Valves for Advanced Emphysema," The New England Journal of Medicine, vol. 363, No. 13, Sep. 23, 2010, 12 pages.
D.H. Sterman, et al., "A Multicenter Pilot Study of a Bronchial Valve for the Treatment of Severe Emphysema," Respiration, vol. 79, No. 3, 2010, 12 pages.
George R. Washko, et al., "Physiological and Computed Tomographic Predictors of Outcome from Lung Volume Reduction Surgery," American Journal of Respiratory and Critical Care Medicine, vol. 181, No. 5, 2010, 7 pages.
Anile et al., "Assessment of intraparenchymal lung collateral ventilation," Thorax, vol. 67, No. 12, 2012, p. 1111.
Ashburner et al., "Voxel-Based Morphometry—The Methods," NeuroImage, vol. 11, 2000, pp. 805-821.
Avants et al., "Symmetric diffeomorphic image registration with crosscorrelation: Evaluating automated labeling of elderly and neurodegenerative brain," Medical Image Analysis, vol. 12, No. 1, Feb. 2008, pp. 26-41, Abstract only.
Batmanghelich et al., "Generative-Discriminative Basis Learning for Medical Imaging," IEEE Transactions on Medical Imaging, vol. 31, No. 1, Jul. 2011, pp. 51-69, Abstract only.
Bodduluri et al., "Registration-based lung mechanical analysis of chronic obstructive pulmonary disease (COPD) using a supervised machine learning framework," Academic Radiology, vol. 20, No. 5, May 2013, pp. 527-536, Abstract only.
Busacker et al., "A Multivariate Analysis of Risk Factors for the Air-Trapping Asthmatic Phenotype as Measured by Quantitative CT Analysis," Chest, vol. 135, No. 1, 2009, pp. 48-56.
Coxson et al., "A Quantification of the Lung Surface Area in Emphysema Using Computed Tomography," American Journal of Respiratory and Critical Care Medicine, vol. 159, 1999, pp. 851-856.

(56) References Cited

OTHER PUBLICATIONS

Friston et al., "Classical and Bayesian Inference in Neuroimaging: Theory," NeuroImage, vol. 16, 2002, pp. 465-483.

Fung et al., "SVM feature selection for classification of SPECT images of Alzheimer's disease using spatial information," Knowledge and Information Systems, vol. 11, No. 2, Feb. 2007, pp. 243-258, Abstract only.

Galban et al., "Computed tomography-based biomarker provides unique signature for diagnosis of COPD phenotypes and disease progression," Nov. 2012, pp. 1711-1715.

Gevenois et al., "Comparison of computed density and macroscopic morphometry in pulmonary emphysema," American Journal of Respiratory and Critical Care Medicine, vol. 152, No. 2, Aug. 1995, pp. 653-657, Abstract only.

Gevenois et al., "Comparison of computed density and microscopic morphometry in pulmonary emphysema," American Journal of Respiratory and Critical Care Medicine, vol. 154, No. 1, Jul. 1996, pp. 187-192, Abstract only.

Global Initiative for Chronic Obstructive Lung Disease, Retrieved from <https://web.archive.org/web/20111130095027/http://www.goldcopd.org/> dated Nov. 30, 2011, 2 pages.

Hersh et al., "Paired inspiratory-expiratory chest CT scans to assess for small airways disease in COPD," Respiratory Research, vol. 14, No. 42, 2013, 11 pages.

Hoffman et al., "Effect of body orientation on regional lung expansion in dog and sloth," Journal of Applied Physiology, vol. 59, No. 2, Aug. 1985, pp. 481-491, Abstract only.

Hogg et al., "Site and Nature of Airway Obstruction in Chronic Obstructive Lung Disease," The New England Journal of Medicine, vol. 278, No. 25, Jun. 1968, pp. 1355-1360, Abstract Only.

Jain et al., "Quantitative computed tomography detects peripheral airway disease in asthmatic children," Pediatric Pulmonology, vol. 40, No. 3, Sep. 2005, pp. 211-218, Abstract only.

Lee et al., "Quantitative Assessment of Emphysema, Air Trapping, and Airway Thickening on Computed Tomography," Lung, vol. 186, 2008, pp. 157-165.

Liu et al., "Discriminative MR Image Feature Analysis for Automatic Schizophrenia and Alzheimer's Disease Classification," Medical Image Computing and Computer-Assisted Intervention—MICCAI 2004, Lecture Notes in Computer Science, vol. 3216, pp. 393-401.

Martinez et al., "Relationship between quantitative CT metrics and health status and BODE in chronic obstructive pulmonary disease," Thorax, vol. 97, 2012, pp. 399-406.

Matsuoka et al., "Quantitative assessment of peripheral airway obstruction on paired expiratory/inspiratory thin-section computed tomography in chronic obstructive pulmonary disease with emphysema," Journal of Computer Assisted Tomography, vol. 31, No. 3, May/Jun. 2007, pp. 384-389, Abstract Only.

Matsuoka et al., "Quantitative Assessment of Air Trapping in Chronic Obstructive Pulmonary Disease Using Inspiratory and Expiratory Volumetric MDCT," AJR, vol. 190, No. 3, Mar. 2008, pp. 762-769.

Mazziotta et al., "A Probablistic Atlas of the Human Brain: Theory and Rationale for Its Development," NeuroImage, vol. 2, 1995, pp. 89-101, Statement of Purpose provided.

McKenna Jr. et al., "Patient selection criteria for lung volume reduction surgery," The Journal of Thoracic and Cardiovascular Surgery, vol. 114, No. 6, Dec. 1997, pp. 957-964.

Papoulis, "Probability, Random Variables, and Stochastic Processes," Third Edition, McGraw Hill, 1991, 678 pages, Preface and Index provided.

Reinhardt et al., "Registration-based estimates of local lung tissue expansion compared to xenon CT measures of specific ventilation," Medical Image Analysis, vol. 12, No. 6, Dec. 2008, pp. 752-763, Abstract only.

Schuhmann et al., "Computed tomography predictors of response to endobronchial valve lung reduction treatment. Comparison with Chartis," American Journal of Respiratory and Critical Care Medicine, vol. 191, No. 7, Apr. 2015, pp. 767-774, Abstract only.

Teo et al., "Creating Connected Representations of Cortical Gray Matter for Functional MRI Visualization," IEEE Transactions on Medical Imaging, vol. 16, No. 6, Dec. 1997, pp. 852-863.

"The Science of Fingerprints: Classification and Uses," US Department of Justice, Federal Bureau of Investigation, 1984, 216 pages, Introduction and Index provided.

Vercauteren et al., "Diffeomorphic demons: Efficient nonparametric image registration," NeuroImage, vol. 45, No. 1, Supp. 1, Mar. 2009, pp. S61-S72, Abstract Only.

Verma et al., "Wavelet Application in Fingerprint Recognition," International Journal of Soft Computing and Engineering, vol. 1, No. 4, Sep. 2011, pp. 129-134.

Yin et al., "Simulation of pulmonary air flow with a subject-specific boundary condition," Journal of Biomechanics, vol. 43, No. 11, Aug. 2010, pp. 2159-2163, Abstract only.

"A Prospective, Randomized, Controlled Multicenter Clinical Study to Evaluate the Safety and Effectiveness of the IBV® Valve System for the Single Lobe Treatment of Severe Emphysema," Spiration, Inc., Retrieved online from <https://clinicaltrials.gov/archive/NCT01812447/2013_03_19>, dated Mar. 19, 2013, 3 pages.

Delaunois, "Anatomy and physiology of collateral respiratory pathways," European Respiratory Journal, vol. 2, No. 9, Oct. 1989, pp. 893-904.

* cited by examiner

SYSTEMS AND METHODS FOR QUANTIFYING REGIONAL FISSURE FEATURES

CROSS REFERENCES

This application claims the benefit of U.S. Provisional Application No. 62/159,098, filed May 8, 2015, the content of which is hereby incorporated by reference in its entirety.

FIELD OF THE INVENTION

Embodiments of the invention generally relate to visualization and characterization of pulmonary lobar fissures and regional fissure features.

BACKGROUND OF THE INVENTION

Severe emphysema is a debilitating disease that limits quality of life of patients and represents an end state of Chronic Obstructive Pulmonary Disease (COPD). It is believed that 3.5 million people in the US have the severe emphysematous form of COPD, and it is increasing in both prevalence and mortality. Current treatment methods for severe emphysema include lung volume reduction (LVR) surgery, which is highly invasive, and can be risky and uncomfortable for the patient. New treatment methods for treating emphysema include bronchoscopy guided LVR (BLVR) devices such as one-way valves that aim to close off ventilation to the diseased regions of the lung, but maintain ventilation to healthier lung. Bronchoscopy-guided techniques have the promise to be less invasive, less costly and more highly accurate treatments for patients with severe disease and improve the quality of life of severe emphysema patients.

Emphysema can present itself in various disease forms (i.e., phenotypes). Predicting the right treatment for these patients at the appropriate time in the disease process likely depends on the phenotype of the disease. Imaging techniques provide an in-vivo mechanism to objectively quantify and characterize disease phenotypes and can be used in the patient selection process for the various procedural options. Quantitative imaging biomarkers can be used to effectively phenotype disease and therefore predict those patients most likely to respond to the targeted treatment options. By triaging patients to the appropriate therapy, there exists a greater promise for a positive impact on patient outcome, reduced healthcare costs, and replacing more invasive procedures like LVR surgery in treating patients with severe emphysema.

Fissures are important anatomical structures within lungs. It is believed that fissures have an effect on regional lung mechanics. For example, adjacent lobes can slide against each other at fissure interfaces, which provide a means to reduce lung parenchymal distortion. In addition, intact fissures play an important role in reducing collateral ventilation among lobes and the spread of diseases. Recently, fissure integrity has emerged as a strong biomarker to predict the response to interventional emphysema therapies including localized lung volume reduction. In short, if the fissure of the lung is intact, an obstructive device like a valve will more likely produce a seal leading to the atelectasis (i.e., collapse) of the diseased lung sub-region. Without an intact fissure, there is a possibility of collateral ventilation and the likelihood of success of the procedure may be reduced. However, accurately detecting and characterizing fissures in diseased lungs is difficult.

Methods of detecting fissures include fitting the existing portions of the fissures to a lobar atlas (as described in E. M. van Rikxoort et al., "A method for the automatic quantification of the completeness of pulmonary fissures: evaluation in a database of subjects with severe emphysema.," European radiology, (2011): 0-7, for example) or by an extrapolation of the existing portion of the fissure to the absent portion (as described in J. Pu et al., "Computerized assessment of pulmonary fissure integrity using high resolution CT," Medical Physics, 37(9), (2010): 4661-4672, for example). However, neither of these approaches makes full use of the anatomic information available in the image data.

SUMMARY

Aspects of the disclosure are generally directed toward systems and methods for quantifying and/or analyzing fissure features from pulmonary scans of a patient, and analyzing the patient based thereon. In some examples, a volumetric pulmonary scan representative of a patient's pulmonary structure can be mapped to a reference domain for comparison to other data sets associated with the reference domain. Methods can include determining one or more fissure features associated with a plurality of regions in the reference domain. In various exemplary embodiments, fissure features can include fissure integrity, fissure curvature, airway related measurements, deformation field, and/or local vascularity related measurements.

Exemplary methods can include comparing the determined one or more fissure features to a plurality of fissure atlases. Each fissure atlas can include statistical data associated with the one or more fissure features for a different population. Such statistical data can be based on regional analysis of volumetric pulmonary scans pf the population. Based on the comparison of the determined one of more fissure features to the plurality of fissure atlases, the patient can be classified into one or more of a plurality of populations.

Exemplary populations can include patients that respond positively to a given therapy, patients who do not respond positively to a given therapy, patients who have a diagnostic symptom, and patients who do not have a diagnostic symptom. In some examples, region-by-region comparison of a fissure feature between the patient's volumetric pulmonary scan to one or more fissure atlases can provide the necessarily information for classifying the patient.

In some examples, a method can include identifying, for a given fissure feature, distinguishing regions in the volumetric pulmonary scans of a plurality of fissure atlases wherein the fissure feature is substantially different among different populations. Such regions can be identified based on comparisons of like regions in different fissure atlases corresponding to different populations. For example, in some embodiments, a region in which a fissure feature is most different between a pair of populations can be considered a distinguishing region with respect to the fissure feature and the pair of populations.

In some embodiments, classifying the patient into one or more of a plurality of populations comprises comparing fissure features of the patient's volumetric pulmonary scan data to like fissure features of fissure atlases in identified distinguishing regions associated with the population(s) and fissure feature. The patient can be classified into the population corresponding to the fissure atlas that best matches the patient's scan data in the distinguishing regions. In some such embodiments, scan data from regions not considered distinguishing regions is omitted from the analysis, minimizing a false classification of the patient based on data potentially unrelated to the classification population.

Systems according to embodiments described herein can include a database comprising a plurality of fissure atlases and a processor configured to classify a first set of volumetric pulmonary scan data into one or more populations.

BRIEF DESCRIPTION OF THE DRAWINGS

The following drawings are illustrative of particular embodiments of the invention and therefore do not limit the scope of the invention. The drawings are not necessarily to scale (unless so stated) and are intended for use with the explanations in the following detailed description. Embodiments of the invention will hereinafter be described in conjunction with the appended drawings, wherein like numerals denote like elements.

DETAILED DESCRIPTION

Figure 1:
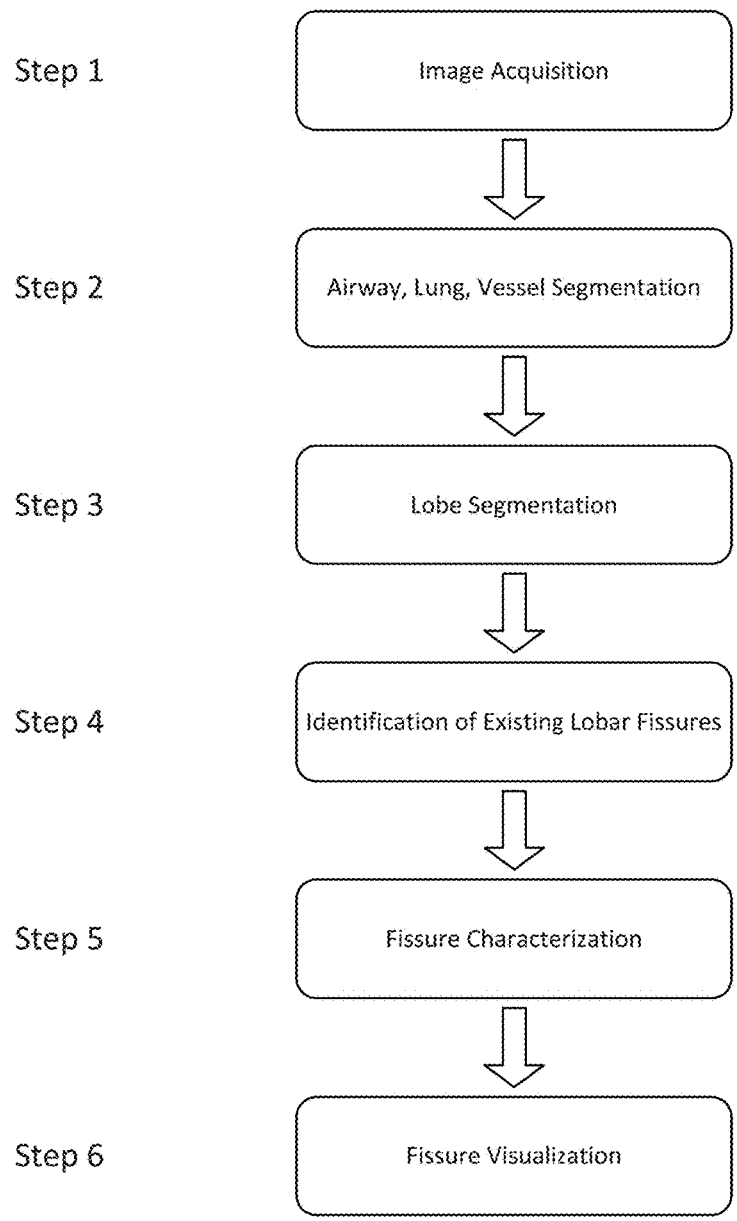
FIG. 1 shows a flowchart of a fissure characterization and visualization method associated with certain embodiments of the invention.

Aspects of the invention describe a process to automate, display, interact with and characterize the fissures of the lung in multiple dimensions. When the human lung is imaged in vivo with an imaging acquisition device, like CT, that image can be reconstructed and evaluated to depict normal and diseased states. Because of the various subclasses of disease and the various depictions (phenotypes) of a disease entity, evaluation of lobular regions of the lung and the fissures separating them are important to accurately characterize disease and predict response to BLVR therapy.

This disclosure includes methods to provide visualization of the fissures in two and three dimensions, define the fissure boundaries, characterize their morphologic characteristics which may be used for identifying a disease phenotype, and visualize regions of intact and missing fissures, and observe the difference between normal and diseased lung in an instantaneous and automated way to enable clinical decision making.

The left and right lungs are each divided into a plurality of lobes by deep clefts, which are the interlobar fissures, referred to herein simply as fissures. The outer surface of the lungs is lined by pleura, including an inner layer which is the visceral pleura which dips into the fissures to surround the lobes. The fissures therefore are the join between the lobes of the lung and are defined by the outermost surface of the lobes and the visceral pleura at the locations where the lobes abut each other. Therefore, although the fissure itself is actually an interface between abutting lobes, it is the very thin layer of the lobar interfaces that can be detected on a volumetric image and is interpreted as being the fissure. The right lung normally includes three lobes (the upper, middle, and lower lobes) which are divided by two fissures, known as the oblique and the horizontal fissure. The left lung normally includes two lobes (the upper and lower lobes) with one fissure, the oblique fissure, between them.

The edges of the lobes and the pleura that lines the lobes define the fissures and separate the lobes such that the ventilation of each lobe separates from that of adjacent abutting lobes. In addition, the pleura normally form a smooth surface, allowing abutting lobes to slide relative to each other during inhalation and exhalation. However, in certain disease conditions, the pleura may become thickened or adherent. In addition, abutting lobes may adhere to each other and the pleura and lung margins that normally define the fissure may be lost. In such locations, the fissure is described as "incomplete," "missing," or "absent" and air can flow between the lobes. Various embodiments described herein identify the fissures using volumetric radiological images such as CT and present them visually in 2D images or in 3D models for a user such as a clinician. In some embodiments, the absent portions of the fissures are also identified and can also be visualized, as by showing the "absent" portions in a color which is distinct from the existing fissures, in a location in which they would normally be present in a complete fissure.

Various embodiments may be performed by a lung visualization system, which may include a processor, such as a processor in a computer, and may also include a visual display such as a monitor or screen. The system may also include instructions included in software (computer readable media), stored in memory of the system, and operable on the processor. The software may include instructions for the processor to perform the various steps and methods described herein, including instructions to receive patient data including volumetric imaging data, analyze the data to characterize the fissures, and display images including three-dimensional images of the fissures resulting from the analysis of the imaging data on the visual display. The software may be incorporated into 3D pulmonary imaging software.

It should also be understood that the three-dimensional images or models described herein are not truly created in three dimensions, because they exist on a flat two-dimensional visual display. Rather, the three-dimensional images described herein use perspective and shading, with the closest portions depicted in the foreground and more distant portions in the background, along with the ability of the user to rotate the images in some cases and/or to see multiple views, to show the entire volumetric volume on the visual display. In contrast, each image in the series of the multi-dimensional volumetric images provided by CT and Mill scans, for example, is a two-dimensional planar image that depicts the tissue present in a single plane or slice. These images are typically acquired in three orthogonal planes, which are referred to as the three orthogonal views and are typically identified as being axial, coronal and sagittal views.

Embodiments of the invention allow the clinician to interact with the three-dimensional model of the lungs and the two-dimensional volumetric images associated with and used to generate the model. For example, the three-dimensional model and the associated two-dimensional volumetric images may be presented in a graphical user interface on a visual display. The user may interact with the graphical user interface, such as by selecting a button, icon, and/or one or more locations on the images or the model or elsewhere using a mouse, stylus, keypad, touchscreen or other type of interface known to those of skill in the art. The creation of the three-dimensional model may be performed by the system including a processor with software (computer readable media) to perform this function as well as software to permit a user to interact with the graphical user interface, to calculate and display desired data and images, and to perform the other functions described herein. The system may further include the visual display on which the graphical user interface is displayed. The three-dimensional model and two-dimensional volumetric images may be provided to a user (such as a clinician or researcher) as a graphical user interface on a visual display, which may be a computer screen, on which the images and data may be manipulated by the user.

Examples of the embodiments may be implemented using a combination of hardware, firmware, and/or software. For example, in many cases some or all of the functionality provided by examples may be implemented in executable software instructions capable of being carried on a programmable computer processor. Likewise, some examples of the invention include a computer-readable storage device on which such executable software instructions are stored. In certain examples, the system processor itself may contain instructions to perform one or more tasks. System processing capabilities are not limited to any specific configuration and those skilled in the art will appreciate that the teachings provided herein may be implemented in a number of different manners.

FIG. 1 shows a flowchart of a fissure characterization and visualization method which may be carried out using software as part of a pulmonary imaging system, for example. At step 1, volumetric radiological images or imaging data of a patient are transmitted to the pulmonary imaging system. Alternatively, the volumetric radiological images or imaging data may already be stored within the memory of the system and may be accessed by the processor. The volumetric radiological images or imaging data may be CT scans, MM scans, and/or PET scans, for example, from which a series of two-dimensional planar images (referred to herein as two-dimensional volumetric images or two-dimensional images) can be produced in multiple planes, for example.

At step 2, the lungs, airways, and/or blood vessels are segmented using the 3D image data. The methods of performing lung, airway and vessel segmentation from the volumetric images or imaging data may be those employed by the Pulmonary Workstation of Vida Diagnostics, Inc. (Coralville, Iowa) and as described in the following references, each of which is incorporated herein by reference: United States Patent Publication 2007/0092864, which is entitled: Treatment Planning Methods, Devices and Systems; United States Patent Publication 2006/0030958, which is entitled: Methods and Devices for Labeling and/or Matching; Tschirren et al., "Intrathoracic airway trees: segmentation and airway morphology analysis from low-dose CT scans," IEEE Trans Med Imaging. 2005 December; 24 (12):1529-39; Tschirren et al., "Matching and anatomical labeling of human airway tree," IEEE Trans Med Imaging. 2005 December; 24 (12):1540-7; Tschirren, Juerg, "Segmentation, Anatomical Labeling, Branchpoint Matching, and Quantitative Analysis of Human Airway Trees in Volumetric CT Images," Ph.D. Thesis, The University of Iowa, 2003; Tschirren, Juerg, Segmentation, Anatomical Labeling, Branchpoint Matching, and Quantitative Analysis of Human Airway Trees in Volumetric CT Images, Slides from Ph.D. defense, The University of Iowa, 2003; and Li, Kang, "Efficient Optimal Net Surface Detection for Image Segmentation—From Theory to Practice," M.Sc. Thesis, The University of Iowa, 2003, for example. Segmentation of the lungs, airways, and vessels results in identification of the lungs, airways, and vessels as distinct from the surrounding tissues and of separation of the lungs, airways, and vessels into smaller distinct portions which may be individually identified in accordance with standard pulmonary anatomy.

At step 3, lobar segmentation is performed. The segmentation of the lungs, airways, and vessels obtained in step 2 can be used to identify and delineate the lobes, again by applying standard pulmonary anatomy. For example, using the identified segments of the airway and/or vessel trees obtained in step 2, the lobes may be segmented and identified by extracting the portions of the airway tree corresponding to particular lobes based on known air way tree structures and connectivity information. The extracted lobar airway tree portions may be further divided into portions corresponding to sub-lobes, again based on known airway and/or vessel tree structure and connectivity information. In this way, the portions of the volumetric images corresponding to lobes and/or sub-lobes can be identified.

Figure 2:
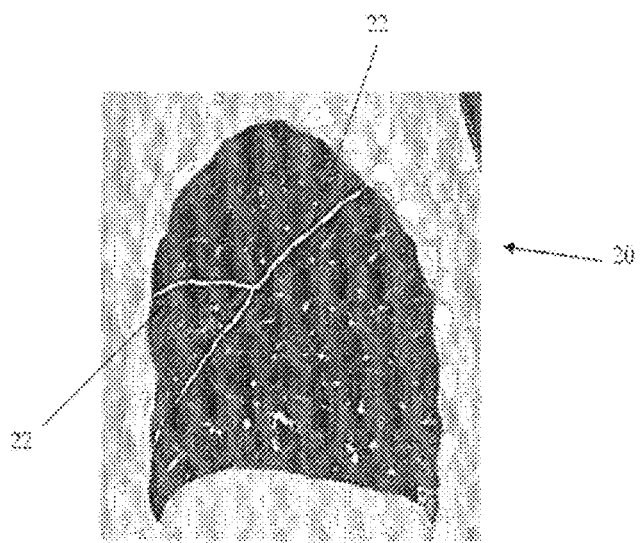
FIG. 2 shows a CT scan in a sagittal view in which the fissures have been enhanced.

In step 4, the lobar fissures portions of the volumetric images are identified by the system. The lobar fissures, as formed by the abutting pleural lining of the lobes, can be seen radiologically on X-ray as well as on two-dimensional, volumetric images such as CT scans. As revealed by the tissues lining the fissures. The fissures may be automatically detected by the system in the volumetric images using known methods or other methods. In some embodiments, identification of the lobar fissures begins with enhancing the fissures to ensure accurate detection. In some embodiments, Hessian-matrix or structure tensor based approaches may be used for identification and enhancement of the fissures, as described in A. F. et al., "Multiscale vessel enhancement filtering," MICCAI. 1998; 1496 (3):130-7, for example. The identified fissures may be enhanced and shown to the user on the volumetric image. An example of this is shown in FIG. 2, which is a sagittal CT scan 10 including enhanced fissure lines 12.

In step 5, the fissures may be characterized. This may be accomplished by combining the information about the lobar segmentation obtained in step 3 with the fissure identification obtained in step 4. The locations at which the lobar regions abut each other may be used to identify the location where a fissure would normally be present. However, in some individuals, portions of the fissure (the tissue lining the fissure) may be absent. Therefore, the normal fissure locations as determined from the lobar anatomy can be compared to the actual fissure locations identified in step 4. If there is a location where a fissure would normally be present as determined by the abutting lobe surfaces, but the fissure identification indicated that there was no fissure present in a portion of or all of that location, then the fissure is described as missing, absent or incomplete in that location. In this way, the pulmonary imaging system not only can identify and highlight existing fissures for users and present them in two-dimensional images and three-dimensional models, but can also identify locations where the fissure is absent. The extent and location of absent fissures can then be used to characterize the patient's disease and to determine appropriate therapeutic approaches. This method differs from existing methods in which absent portions are calculated by either fitting the existing portions of the fissures to a reference atlas (van Rikxoort et al, 2011) or by an extrapolation of the existing portion of the fissure to the absent portion (Pu, et al., 2010). In the lobar atlas approach, a reference atlas is created using the fissure locations of a group of subjects. The fissures of an individual patient can be compared to the reference atlas to predict the locations of absent portions of the fissures. This method relies on consistency of anatomy among individuals, which may not be accurate, particularly in the presence of severe disease which can dramatically change fissure patterns. In the extrapolation based method, the location of missing fissures is estimated by extending existing fissures into the missing spaces. This method may cause unpredictable errors, particularly in patients having low fissure completeness. Therefore, although these and other alternative methods of identifying missing fissures may be used, these other approaches do not make full use of the anatomic information available in the CT image data in the way that the identification of abutting fissures does.

Once the locations of existing fissures and absent fissures have been identified, they can be presented visually to a user in two dimensions, such as on a CT scan, or in three dimensions, such as in a three-dimensional model. This step of fissure visualization is indicated at step 6 on FIG. 1. In some embodiments, the visual presentations can either show only the existing fissures, with gaps where the fissures are absent. In other embodiments, only the areas of missing fissure may be shown. In still other embodiments, the areas of missing fissures can be shown, with the missing fissure being shown as the way the fissure would look if it were present. In some embodiments, the missing fissure is shown in a way that contrasts with the existing fissure, to clearly indicate that, although a fissure is shown, the displayed fissure actually represents an area of missing fissure. For example, the missing fissure portions may be shown in a different color than the existing fissure portions. The fissures may be shown as a three-dimensional model in isolation or in combination with other components of the lungs such as the airway tree, parenchyma, and/or the vessels.

Figure 3:
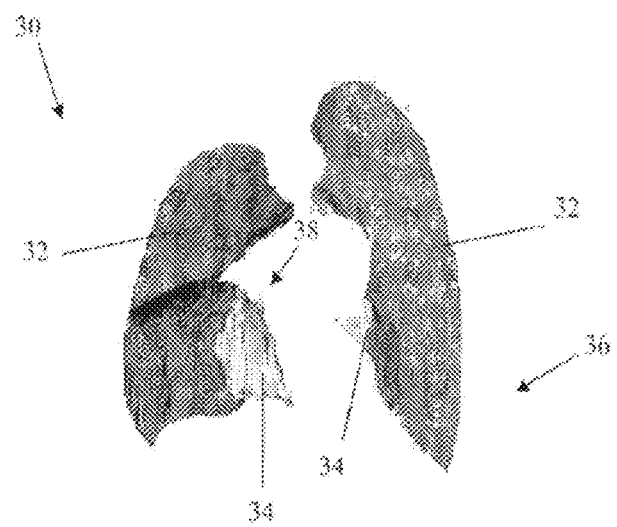
FIG. 3 shows three-dimensional models of surface rendering of fissures of an emphysema patient in accordance with certain embodiments of the invention.

An example of a three-dimensional model of a patient's fissures 30 in isolation is shown in FIG. 3, with the existing fissure portions 32 shown in a first color represented by dark gray and the missing fissure portions 34 shown in a second color represented by light gray. In this patient, who suffers from emphysema, the left oblique fissure 36 is more than 95% complete, while the horizontal fissure 38 is only about 70% complete.

Figures 4A, 4B:
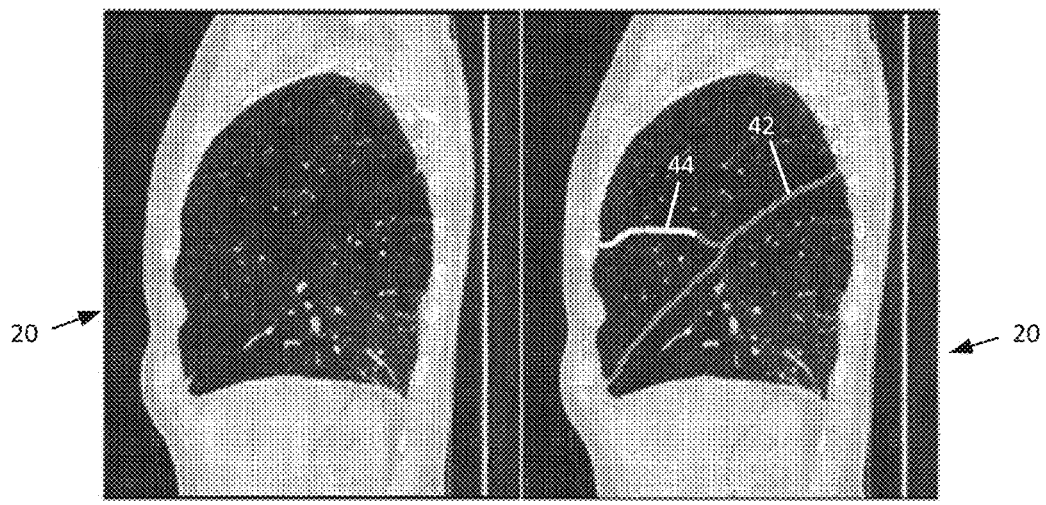
FIG. 4A shows an example of a sagittal CT image of the right lung without fissures identified and highlighted in accordance with certain embodiments of the invention.
FIG. 4B shows an example of a sagittal CT image of the right lung with fissures identified and highlighted in accordance with certain embodiments of the invention.

In FIG. 4B, the existing 42 and missing portions 42, 44 of a patient's fissures are shown in two dimensions, overlaid on a sagittal view CT image 20 of the right lung of a patient. The existing fissures 42 are shown in a first color represented by dark gray, while the missing portions 44 are shown in a second color represented by white. For purposes of comparison, the same CT image is shown in FIG. 4A without the fissure overlay. It can be appreciated how much more difficult it is to determine the location of the fissures, and what portions are absent, without the assistance of the fissure visualization provided in FIG. 4b.

Figure 5:
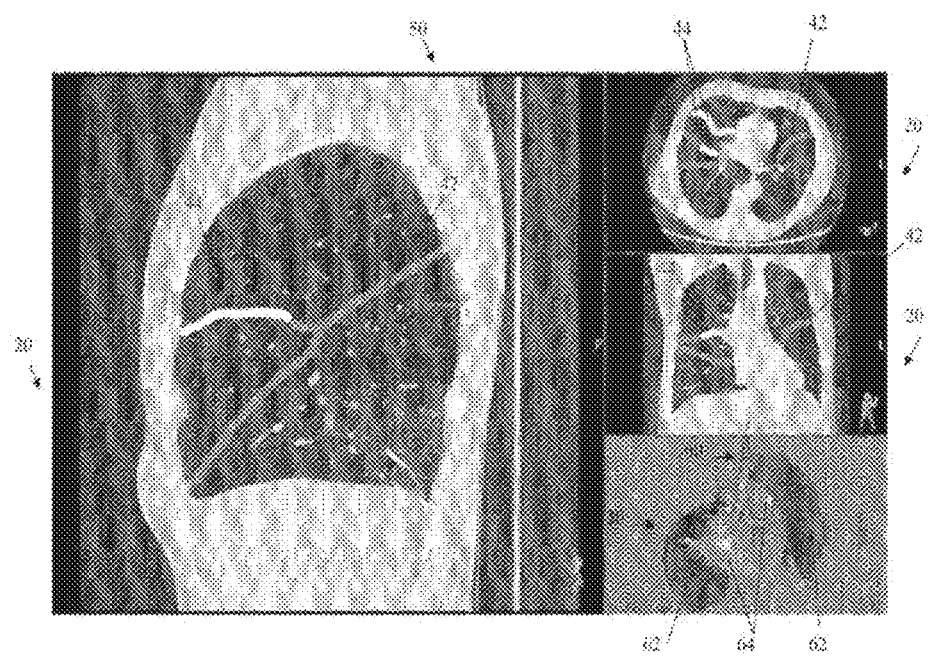
FIG. 5 shows an example of a screen shot including highlighting of the fissures in various two-dimensional CT images and a corresponding three-dimensional volume rendering in accordance with certain embodiments of the invention.

FIG. 5 is an example of fissure visualization in multiple views, as it may be presented to a user in a graphical user interface and therefore represents a screen shot 50 that may be provided by the pulmonary imaging system. It can be seen that the screenshot 50 includes CT images 20 in the three orthogonal views: a sagittal view, an axial view, and a transverse view. In each of the CT images 20, the existing and missing portions of the fissures 42, 44 are enhanced using a different color, with a first color represented by dark gray indicating the existing fissure 42 and a second color represented by white indicating the missing fissure 44. The user may have the option to select different images to be presented on the display, such as by moving from one image to another in a series for a particular view. The screenshot 50 also includes a three-dimensional model of the fissures 30 along with a model of the airway tree 60, constructed from the analysis of the two-dimensional volumetric data, with the areas existing and missing fissures 62, 64 shown in different colors corresponding to the colors used in the two dimensional images and represented by dark gray and light gray for purposes of visualization in this figure.

In addition to using the fissure information to visually enhance or display the fissures, the fissure information can also be used to characterize the fissures, as indicated at step 5 of FIG. 1. Such fissure characterization can include characterizing the location of disease, disease heterogeneity, and/or extent of disease (such as the Global Initiative for Chronic Lung Disease, or GOLD, classification system), for example.

In some embodiments, a fissure integrity score may be calculated to characterize the fissure of a portion thereof. The fissure integrity score may be calculated as the incompleteness percentage (IP) or conversely as the completeness percentage (CP). These values may be calculated using the total area of existing fissure and of the absent fissure portions determined as described above using the following equations:

$$IP (\%) = 100 * [1 - ExistingFissure/(ExistingFissure + AbsentFissure)]$$

$$CP (\%) = 100 * ExistingFissure/(ExistingFissure + AbsentFissure)$$

These measurements can be made for a single fissure, for a selected portion of a fissure such as only a portion abutting a particular lobe or sub-lobe, or for a combination of fissures or selected portions of fissures. The choice of which portion of the fissure to assess may be determined by the possible locations of therapeutic interventions such as BLVR surgery. That is, the fissure integrity score may be calculated for those fissures or portions thereof which abut a lobe or sub-lobe for which BLVR therapy is being considered. For example, if bronchoscopy guided BLVR therapy is being considered for either the left upper lobe or the left lower lobe, the fissure integrity score may be calculated for the entire left oblique fissure, because this fissure abuts both of these lobes along its entire length. If the use of BLVR therapy is being considered in the right lower lobe, the fissure integrity score may be calculated based on the entire right oblique fissure. If BLVR surgery is being considered for the right upper lobe, the fissure integrity score may be calculated from the combination of the upper part of the oblique fissure (only the portion of the fissure abutting the right upper lobe) and the entire horizontal fissure. If BLVR surgery is being considered for the right middle lobe, the fissure integrity score may be calculated for a combination of the lower part of the oblique fissure (only the portion of the fissure abutting the right middle lobe) and the entire horizontal fissure.

Because the fissure integrity score provides a numerical assessment of how intact (or not intact) the fissures are, it provides a global quantitative assessment of possible collateral ventilation. For example, if the completeness percentage is 100%, the fissure is intact and there is likely no collateral ventilation between adjacent lobes. BLVR therapy is therefore more likely to be successful. On the other hand, of the fissure integrity score indicates that the fissure completeness is low, collateral ventilation may occur through the missing areas of fissure and the outcome of BLVR therapy may be less successful.

In some embodiments, the fissure integrity score may be used to decide whether or not to proceed with BLVR therapy and in which lobes or sub-lobes to perform such therapy. For example, a fissure integrity score cut-off or threshold may be used for therapeutic decision making. A patient with a completeness percentage below the threshold may be ineligible for BLVR surgery for the corresponding portion of the lung. Likewise a patient with an incompleteness percentage above the threshold may be ineligible for BLVR surgery for the corresponding portion of the lung. The fissure integrity score may therefore be used to triage patients as being ineligible for, or possibly eligible for, BLVR therapy.

In some embodiments, the relationship between the existing and absent fissures and other normal or abnormal lung structures can also be evaluated and measured. For example, the lobes of the human lungs can be further dived into bronchopulmonary segments, also called sub-lobes. Each sub-lobe is supplied by one bronchus. There are typically 10 sub-lobes in the right lung (3 in upper lobe, 2 in middle lobe, 5 in lower lobe) and 8-10 sub-lobes in the left lung (4-5 in upper lobe, 4-5 in lower lobe). Depending on their locations, the surfaces of some sub-lobes may be located at fissure locations, thus contacting the fissures at such locations, or they may not abut the fissures. In some embodiments, the portion of a fissure contacting a sub-lobe may be identified and characterized as separate from the remainder of the fissure. For example, characterization of a fissure in a sub-lobe contacting area can be performed (such as the completeness percent or the incompleteness percent) and the portions of fissures in contact with different sub-lobes can be visually distinguished from each other when displayed for user.

Figure 6:
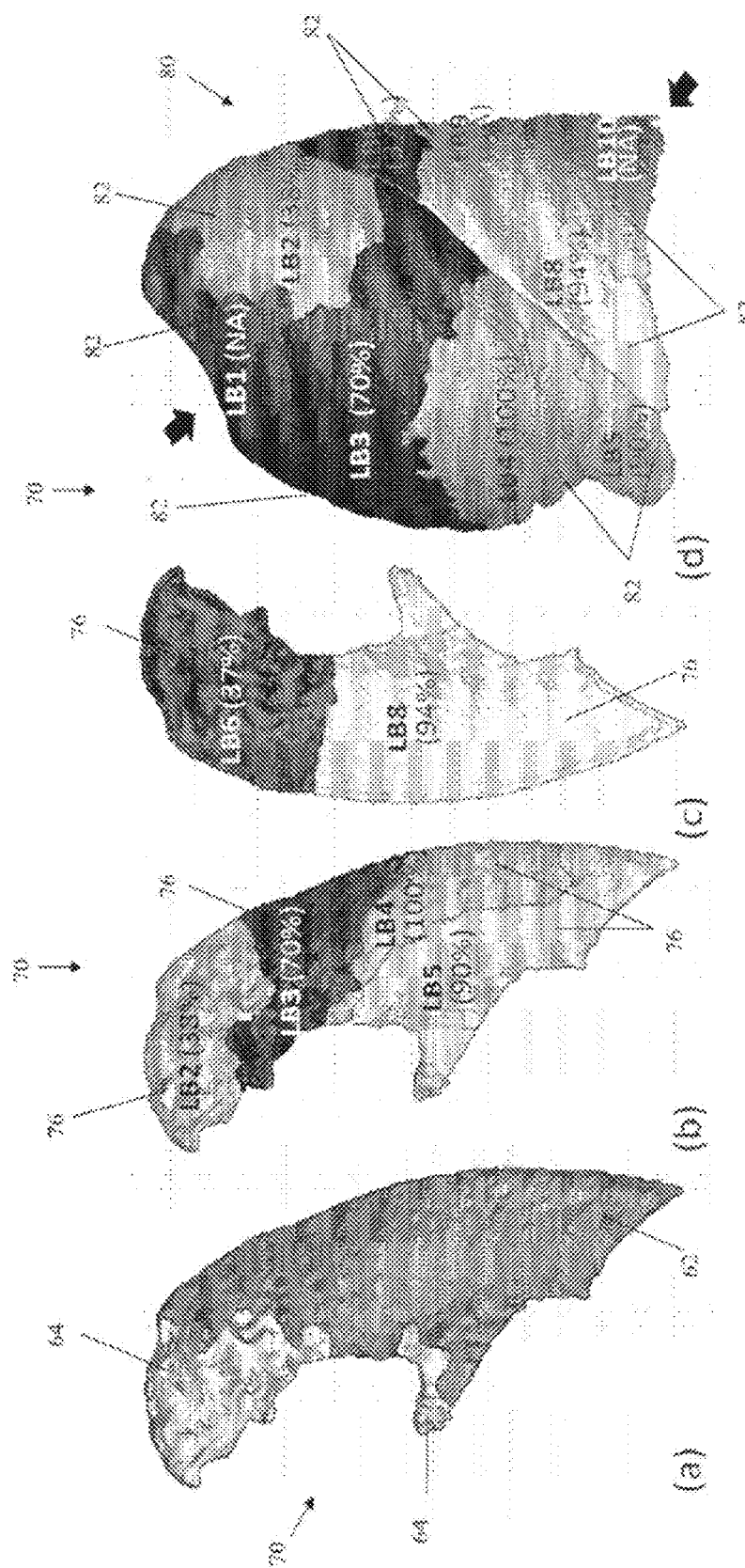
FIG. 6 shows an example of three-dimensional models of a fissure (a)-(c) and of the sublobes surrounding the fissure (d).

A visual presentation of the portions of fissures which contact various sub-lobes can be provided to clinicians as an indication of the fissure integrity at a sub-lobar level. An example of this is shown in FIGS. 6 (a)-(d) in which 3 dimensional models of portions of a fissure are shown in a variety of ways that such models may be provided to a clinician, with the sub-lobe labels having been identified and displayed with the fissure portions based on the sub-lobe associated with (contacting) that portion of the fissure. In these figures, the portions of the fissures contacting different sub-lobes are each colored differently, represented by different shades of gray in the figures, in order to distinguish them from each other, and different colors are also used to distinguish existing from missing fissure portions. In FIG. 6(a) the existing portions 62 left oblique fissure 70 are shown in dark gray while the absent portions 64 shown in light gray. In FIG. 6(b), the left oblique fissure 70 is again shown, with each area of contact of the sub-lobes 76 of the left upper lobe with the fissure distinctly colored and labeled. Similarly, in FIG. 6(c), the left oblique fissure is shown (as seen from below, the opposite side as shown in FIG. 6(b)) with each area of contact of the sub-lobes 78 of the left lower lobe distinctly colored and labeled. In FIG. 6(d), the entire left lung is shown as a three-dimensional model 83, with each of the sub-lobes 82 separately and distinctly colored (shown in shades of gray) and labeled with a sub-lobe label 84 and with the fissure completeness score 86 for each portion of the fissure in contact with that sub-lobe.

This information relating to the completeness percentage of the portion of a fissure contacting a sub-lobe may be used in combination with other information, such as density based emphysema measurements, which may be specific to the lobes or sub-lobes, for example, to guide BLVR treatment planning. This sub-lobe fissure information can then be used as a degree of the influence of fissure integrity on sub-lobes. If treatment is being planned for a particular lung volume such as a lobe or sub-lobe, and if a portion of the fissure contact with that lung volume has a low fissure integrity, the treatment of that lung volume may not be effective or may be less effective than desired due to collateral ventilation from across the fissure. In such cases, the treatment plan may be modified to manage the portion of the fissure having low fissure integrity. For example, the treatment plan may include targeted treatment of the particular lung volume as well as a sub-lobe or sub-lobes on the contralateral side of the fissure from the particular lung volume and adjacent to the portion of the fissure having low fissure integrity. In this way, collateral ventilation of the particular treated lung volume can be prevented by targeted treatments to lung lobes or sublobes across from each other on both sides of a portion of the fissure having low fissure integrity.

Other useful information which can be determined based on the fissure identification includes the spatial relationship between fissure locations and the regions of the lung affected by emphysema, for example. For example, the distance of fissures (both intact and missing portions) from the centroids of regions of emphysema can be calculated. The orientation of the fissures relative to the regions of emphysema can also be determined. This distance and orientation information can be used to predict the impact of fissure integrity on treatments in the corresponding regions of emphysema. Additionally, the information may help with characterizing the emphysema and understanding the impact of fissure integrity on the progress of the emphysema.

Figure 7:
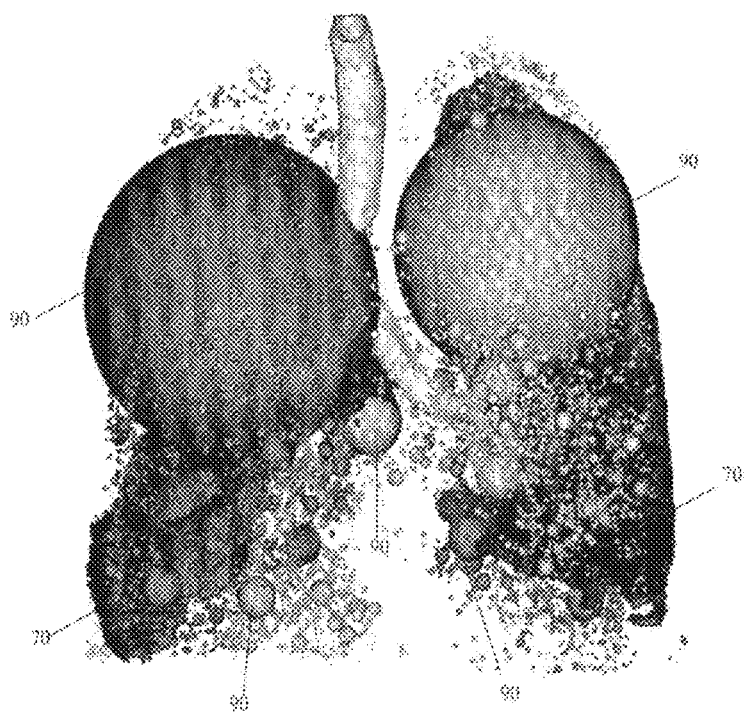
FIG. 7 shows an example of visualization of the spatial relationship between fissures and regions of emphysema in a three-dimensional model in accordance with certain embodiments of the invention.

FIG. 7 is an example of a visual representation of the spatial relationship between fissures 70 and regions of emphysema as it may be provided to a clinician in various embodiments. The visual representation can be used by the clinician to visually assess the local influence of emphysema on fissure integrity. In FIG. 7, the regions of emphysema are symbolically represented by spheres 90 with radii reflecting the sizes of those regions, though other types of visual representations may alternatively be used.

Figure 8:
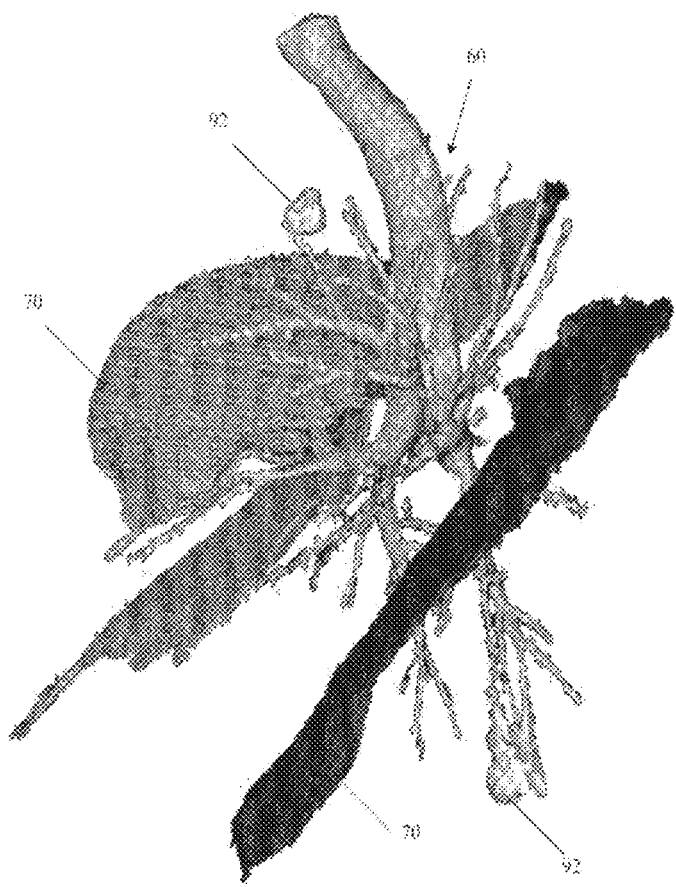
FIG. 8 shows an example of visualization of the spatial relationship between fissures and tumors in a three-dimensional model in accordance with certain embodiments of the invention.

Other information which can be determined using the fissure identification includes the spatial relationship between fissures and tumors, which may have an impact on patient prognosis. For example, recent findings suggest that the presence of tumor invasion through a fissure has a significant negative impact on long-term survival, due perhaps to the rapid spread of such tumors. Thus, it is useful to know the relative locations of fissures and tumors, the distance between them, and whether or not the tumors invade the fissures. Various embodiments therefore identify the locations of tumors and fissures, provide images such as the 3 dimensional model of the fissures 70 and airways tree 60 shown in FIG. 8 in which the tumor 92, fissures 70, and the airway tree 60 can be seen, and/or calculate the nearest distance between the fissures 70 and the tumor 92. Since tumors invading through the fissures have a significant effect on long-term survival, it is important to visualize the spatial relationship between fissures and tumors. In the example shown in FIG. 8, it can be seen that both tumors 92 are confined to a single lobe and they do not invade the fissures 70.

In addition, local and global measurement of fissure integrity can also be utilized to predict the spread of diseases such as cancerous tumors. Other measurements which may be made by the system in various embodiments include the distance between the fissures and anatomical landmarks or locations such as the lung apex, the diaphragm, and the ribs, for example. In addition, these measurements can be performed at different levels of lung inflation, to provide information about, and to help better understand, lung mechanics in both normal and diseased lungs.

As discussed above, the fissures are the interface between the lobes of the lungs and they are lined by the pleura. An analysis of the fissures can therefore include characterization of the pleura itself. For example, pleural thickening can occur in certain disease conditions, and in some cases is due to inflammation. Such pleural thickening can result in changes in the intensity distributions and thickness of fissure surface. For example, portions of the fissure may have an abnormal intensity on volumetric imaging which may be indicative of the presence of disease or fluid. Various embodiments may therefore identify the intensity, such as in Hounsfield Units (HU), of the fissures and of the various portions of the fissures if the intensity is not uniform. Various embodiments may therefore provide measurements of the intensity distribution and the thickness of the pleura, or can assist a clinician in making these measurements, to provide further information about and characterization of the associated disease.

In some embodiments, the shape of the fissure may be determined by the system. Fissure shape can be changed due to lung disease, such as emphysema. Thus, analysis of fissure shape can also be useful in characterizing lung disease. The shape analysis may include, but is not limited to, principal component analysis and surface curvature measurement, for example. These results may be provided in comparison to normal results, for example, to help identify areas of abnormality since the normal shape can be altered due to some diseases.

In some embodiments, the topology of the fissure surface may be characterized. The topological information may include, for example, the number of holes (incomplete portions) in the fissure, which could be caused by or associated with a vein crossing the fissure.

Figure 9:
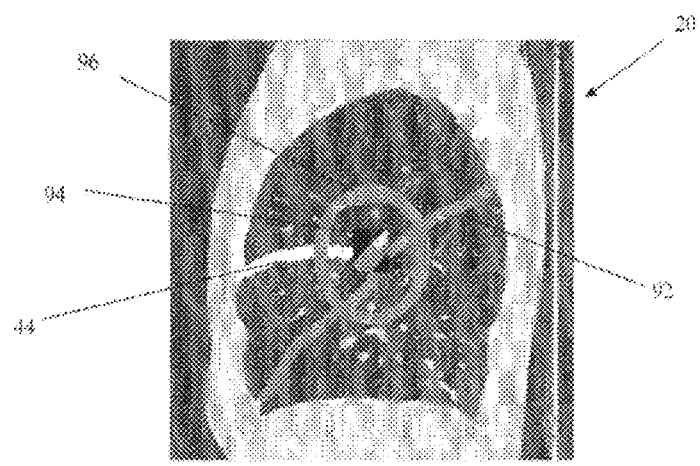
FIG. 9 illustrates a fissure editing tool in use to revise the identification of a portion of a fissure as complete or incomplete on a CT image.

In some embodiments, a clinician may interact with the visual display to identify the fissures manually or to edit the fissures that were automatically identified by the system. An example of an editing tool icon 94 is shown in FIG. 9, in which a sagittal CT image 20 of the lungs is shown. The editing tool 94 can be used to edit the enhanced fissure line 22, such as to change the characterization of the identified fissure from existing fissure 42 to incomplete fissure 44 or vice versa. The editing tool, the icon for which may appear differently from that shown in FIG. 9, may allow a user to change the identification of the voxels at the fissure location, relabeling them as either existing fissure or incomplete/missing fissure.

In some embodiments, the process of editing a fissure using a fissure editing tool may include the following steps. First, a user may select a fissure editing tool for use in a two-dimensional image. The two-dimensional image may include identification of the fissure locations as existing or incomplete, as automatically identified by the system, which may be shown enhancing the fissure by using colors such as blue for existing and green for missing fissure. The user may then position to the editing tool icon at a selected a location in the two-dimensional image including the automatically identified existing and missing fissure. The user may then direct the system to change the fissure identification (from existing to incomplete, or from complete to existing) using the tool. For example, the user may click and drag a mouse to move the corresponding tool icon on the display, at the location of the portion of the fissure for which the user wishes to change the fissure identification. During use, the tool editing icon may appear in a color matching the color of the new (revised) state of the fissure, such as a first color or shade of gray such as light gray for intact or a second color or shade of gray such as dark gray for missing fissure, for better visualization of the underlying CT data. The fissure label (existing or missing) in the edited image and neighboring images will be automatically updated according to the size of the 3D sphere. An example of this is shown in FIG. 9 in which circle 96 represents the central cross-section of the 3-dimensional volume within which the fissure identification will be changed, if so directed by the user. The color change may occur immediately while the user is interacting with the image, or may occur when the user indicates that editing is complete, such as by unclicking the mouse.

Figure 10:
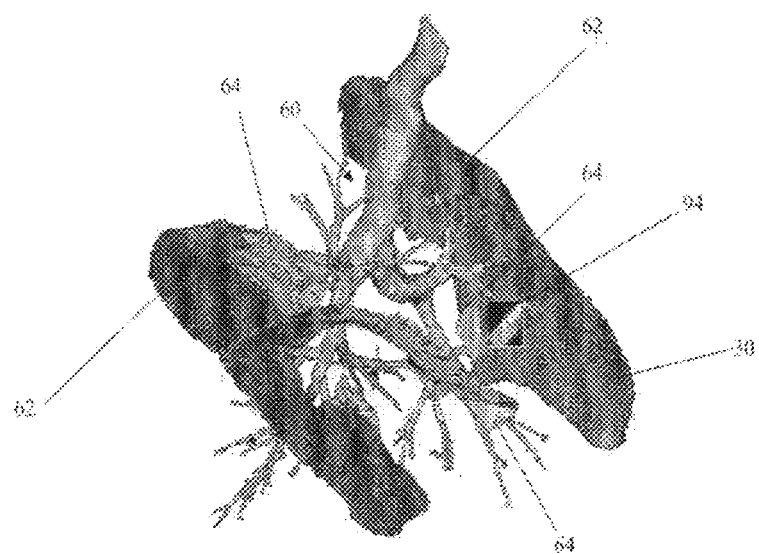
FIG. 10 illustrates a fissure editing tool in use to revise the identification of a portion of a fissure as complete or incomplete on a three-dimensional model of the fissure.

Fissure editing may also be performed by a user by interacting with a three-dimensional model of the fissures produced by the system. An example of this is shown in FIG. 10, in which the editing tool icon 94 is shown in the 3D model of the fissures 30. The model also includes a 3D model of the airway tree 60. The user may edit the fissure characterization using the following steps. First, the user may select the editing tool for use in the three-dimensional model, which displays both existing and incomplete portions 62, 64 of the fissures as automatically identified by the system and/or previously edited by a user. The user may place the editing tool icon 94 on a selected location on the fissure model 30. The user may then apply the tool to the fissure to change the identification of the fissure location as existing or incomplete, such as by clicking and dragging the icon using a mouse, at the fissure location as described above for editing the two-dimensional image. In response, the system may change the fissure characterization, and likewise change the fissure color shown in the model 30, to indicate the revised fissure characterization.

The use of the pulmonary visualization system which includes automatic lobar fissure identification, visualization, and characterization as described herein provides several advantages. The system may provide a priori knowledge to predict the response of a patient to a bronchoscopically-guided procedure such as a BLVR procedure. It may also provide an easily recognizable visual display of completeness and incompleteness of the lobar fissure, such as through the use of color coding. It may also provide an easily recognizable visual display of the spatial relationships between fissures and normal and abnormal lung structures including the airway tree, the lobes, the sub-lobes, the fissures, regions of emphysema, and tumors, for example. In addition, it may detect and identify normal and abnormal regions of the lungs and fissures and link two-dimensional data and images to multidimensional visualization and measurements. In some embodiments, it may offer "on-demand" measurement of fissures for purpose of immediate evaluation of normal and diseased states, determination of the appropriateness of a proposed procedure, and procedure planning. The automation of the measurement of the fissure integrity may provide enhanced clinical utility by allowing easier, faster, and more accurate decisions, thereby saving time, money and potentially lives.

Various embodiments may be used by physicians to predict the response of a patient with emphysema or other lung disease to a proposed procedure, such as the implantation of a device or other BLVR treatment. Treatment planning and determination of the most appropriate device therapy may be optimized by predicting response. For example, thoracic surgeons may use the information for treatment planning for lung volume reduction surgery. Radiologists and pulmonary clinicians may use these characterizations to determine the appropriate patients to triage to endobronchial BLVR therapy. Pulmonary clinicians may use the information to plan procedures for BLVR therapies and to evaluate treatment response.

With regard to the prediction of collateral ventilation, it is noted that such a prediction may be considered as intralobar or interlobar collateral ventilation. Intra-lobar collateral ventilation may occur through the accessory pathways of the lungs including the intra-alveolar pores of Kohn (the Pores of Kohn take their name from the German physician Hans Kohn [1866-1935] who first described them in 1893), the bronchioalveolar communication of Lambert and the intrabronchiolar pathways of Martin. In 1955, Lambert discovered that there were accessory bronchioloalveolar communications extending from respiratory bronchioles to alveolar ducts and sacs subtended by the bronchiole. Later, Martin was able to pass polystyrene spheres up to 120 microns in diameter from one segment of the canine lung to another, through the collateral channels. (See, e.g., Menkes H, Traystman R, Terry P., Collateral ventilation. Fed Proc. 1979 January; 38(1):22-26, hereby incorporated by reference). In certain conditions, such as emphysema, these accessory pathways can become enlarged and airway obstruction can increase expiratory resistance, leading to the passage of air as intralobar collateral ventilation from one lobule to another. Interlobar collateral ventilation may occur when portions of the interlobar fissures are absent or when the adjacent lobes become fused to each other, resulting in an incomplete fissure and allowing air communication between the lobes at those locations.

In some embodiments, fissure integrity data as herein described can be analyzed in conjunction with treatment efficacy data of patients that have undergone a procedure such as LVR therapy. Statistical analysis of such data can provide greater insight as to whether particular fissure sections may be more reliable at predicting treatment efficacy than others. That is, based on air-flow physics, various portions of the fissure surface may contribute differently to collateral ventilation. If so, the prediction of response to LVR treatments may be improved based on more regional information of fissure completeness.

However, analysis of a plurality of patients may be difficult, as the overall lung structure (e.g., shape and size of lungs, lobes and sub-lobes) may vary from person to person and change based on the level of inspiration. As previously described, a collection of data from a variety of patients may be used to build a reference atlas or a set of reference atlases that are created using the fissures or other pulmonary structures from one or various groups of subjects. For instance, in some embodiments, 3D pulmonary data of lungs or fissures of a given patient can be registered to the reference domain on a voxel-by-voxel basis.

Each entry in the atlas may be registered to the reference domain so that voxel-based statistical analysis may be performed among entries in the atlas while referring to the same physical location within the lungs. That is, after registration, a location identified in one patient in an atlas will have a corresponding location in any other subjects in the atlas. In some examples, the reference domain can have pre-defined lung structures including lungs, lobes, sub-lobes, fissures, and the like of a reference patient. In some such examples, the reference patient may be a healthy patient or a patient with mild disease and nicely defined fissure surfaces or other lung structures.

Figure 11:
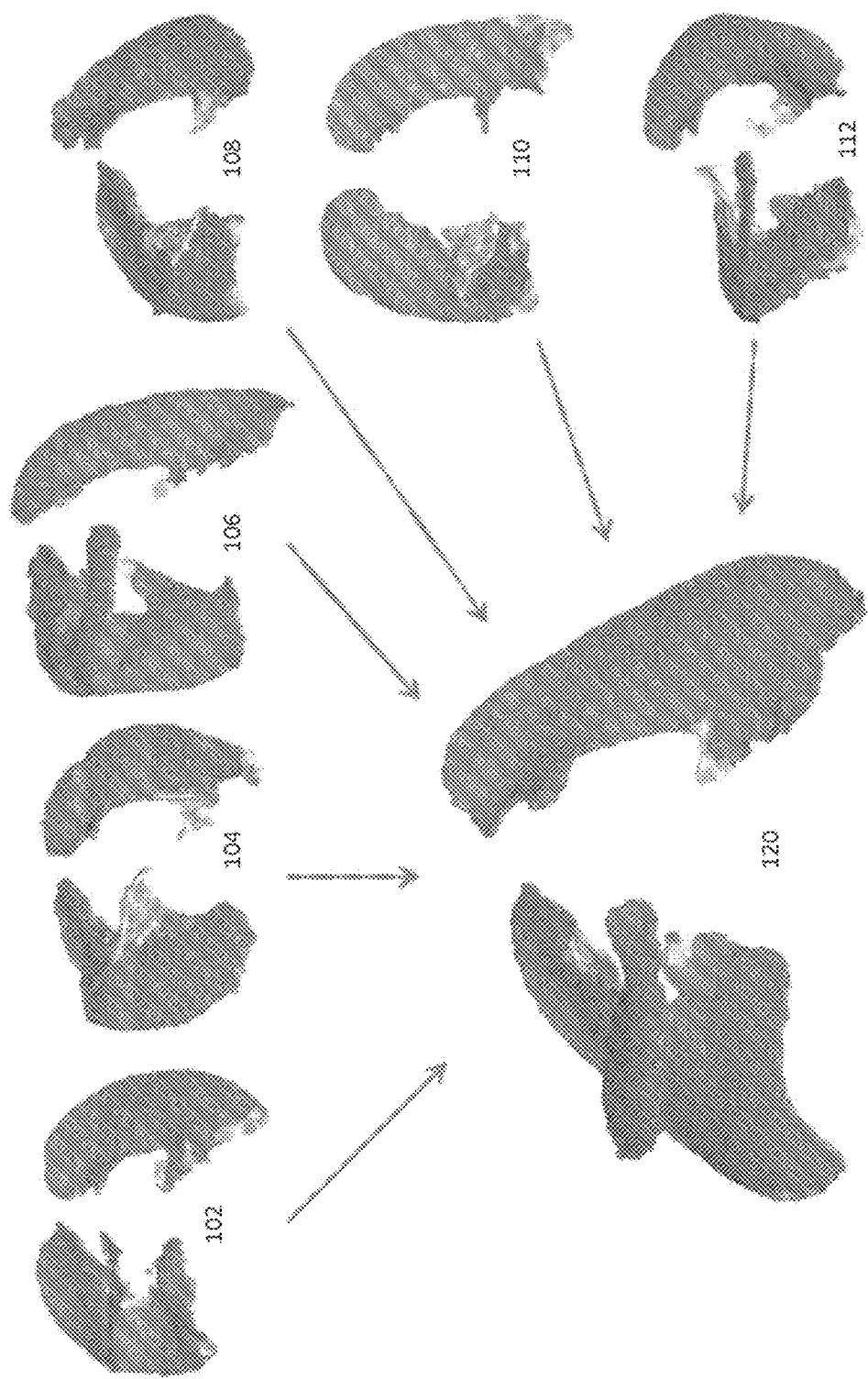
FIG. 11 shows a series of exemplary 3D fissure surface models from different patients.
Figure 12:
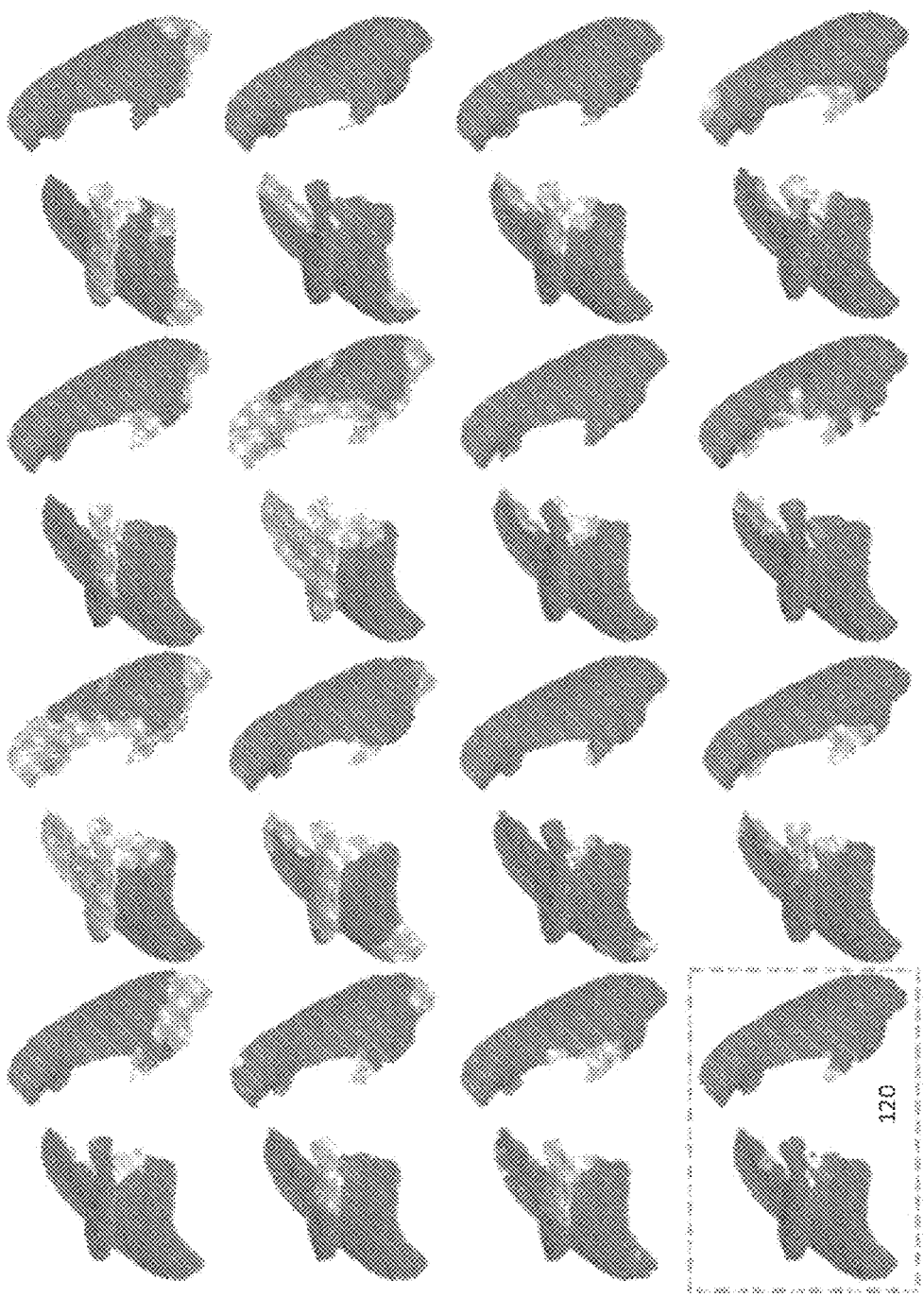
FIG. 12 shows a series of fissure atlas entries registered to a single reference model.

FIGS. 11 and 12 illustrate exemplary registration of 3D fissure surface models from an atlas into a reference domain. FIG. 11 shows a series of exemplary 3D fissure surface models 102-112 from different patients. In each model, dark gray surface indicates the complete portions of a fissure, while the light gray surface indicates the incomplete portions. It is evident from the models that each patient has a unique fissure makeup. It is also evident that the overall lung structure (e.g., shape, size, etc.) varies widely from patient to patient. Accordingly, it may be difficult to directly compare fissure information between, for example, models 106 and 112 based on the images of FIG. 11. However, as previously described the fissure surface models 102-112 may be registered to a reference domain 120 to allow direct voxel-by-voxel comparison of fissure characteristics.

FIG. 12 shows a series of atlas entries registered to a single reference model. As shown, a variety of models in the atlas include fissure information as described above with reference to FIG. 11. However, in the illustrative example of FIG. 12, each entry has been registered on a voxel-by-voxel basis to the reference domain 120. That is, the overall shape and structure of each of the registered models was warped into the reference domain 120, but retains its own fissure integrity data. By establishing the spatial correspondences among fissures from different subjects, one can evaluate the statistical differences in fissure integrity, and other fissure properties amongst a given population. For example, such data can be statistically analyzed among various populations including but not limited to: LVR responders, LVR non responders, subjects with or without collateral ventilation, subjects with various degrees of pulmonary disease (COPD, asthma, etc.). It will be appreciated that, with respect to FIGS. 11 and 12, while various portions of the image represent fissure completeness, other fissure characteristics, such as curvatures, distance map to other lung structures, etc., may be represented in the fissure atlas.

Once the atlas is built (e.g., once plurality of scan data has been registered to the reference domain), statistics from a given population may be analyzed. For example, in some embodiments, entries in the atlas can be divided into two categories: patients who responded to a particular treatment (responders) and patients who did not (non-responders). In other examples, responders and non-responders can be divided into separate atlases. Fissure characteristics such as integrity data can be analyzed on a voxel-by-voxel basis to determine the likelihood that, among patients in one particular category, certain fissure characteristics are present. In some examples, the likelihood that the fissure in a given voxel is intact can be determined. For example, given a group of 100 responders to a treatment and a voxel or region $V_1$ located on the fissure, it can be determined how many of the 100 responders had a complete fissure represented at $V_1$. This number may be referred to as "fissure integrity likelihood". Other likelihood determinations related to additional fissure characteristics are possible.

Figure 13:
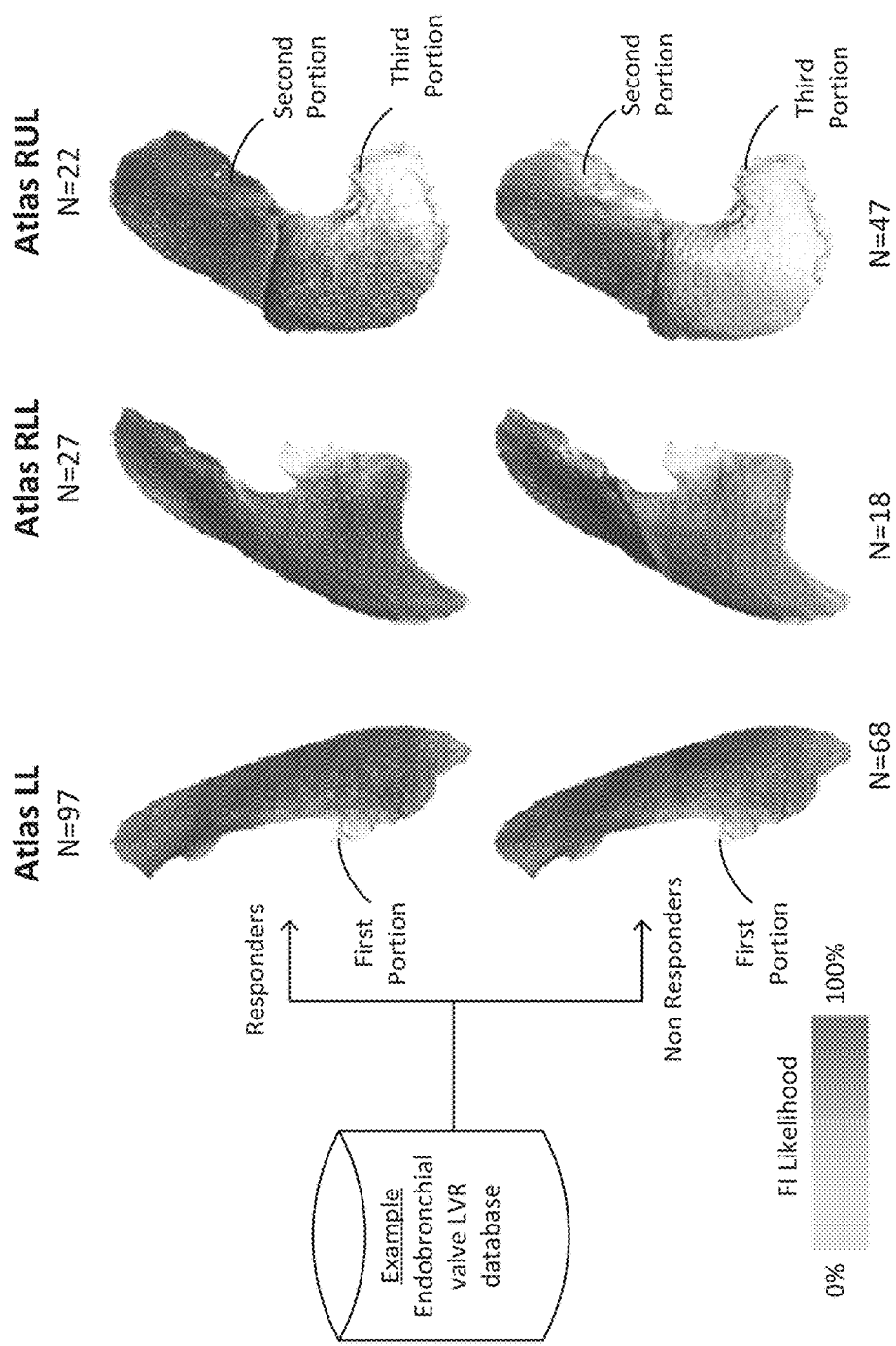
FIG. 13 is a visual representation of the relationship between the fissure integrity likelihood and response to a treatment according to some embodiments.

FIG. 13 is a visual representation of the relationship between the fissure integrity likelihood and response to a treatment. For example, a series of patient scans can be organized into a series of atlases with each of the atlases containing scans having like properties. Such properties can include responders to a particular therapy (or non-responders), diseased patients, healthy patients, patients with specific diseases, patients with certain stages or severity of a disease, and the like. In some instances scans can be divided into atlases corresponding to such categories for direct comparisons with other categories, such as healthy vs. diseased patients, patients with a first disease vs. patients with a second disease, or patients at various stages of a disease. In the illustrated example, the upper section of FIG. 13 includes atlases of the left lung (LL, either left lower or left upper lobe), the right lower lobe (RLL), and the right upper lobe (RUL) for responders to endobronchial valve therapy treatment. Each atlas is statistically analyzed to determine the fissure integrity likelihood at each voxel. The lower section of FIG. 13 shows similar data for non-responders. In the illustrated embodiment, dark gray sections indicate voxels representing portions of the fissure that were intact in most of the patients in the group. Light gray sections indicate voxels representing portions of the fissure that were not intact in most of the patients in the group.

Voxel-by-voxel comparisons of fissure integrity likelihood scores for responders and non-responders may allow for visualization of which portions of a fissure are important for the efficacy of therapy. For instance, it can be seen that there is a low fissure integrity likelihood corresponding to a first portion of the LL in non-responders. At first, this may suggest that the integrity of the first portion of the LL includes an important fissure section for the efficacy of the therapy. However, analysis of the LL in responders to the therapy reveals that patients may in fact respond to the therapy despite a low fissure integrity likelihood at the first portion. Accordingly, a patient having low fissure integrity at the first portion of the left lobe may still respond to endobronchial valve therapy. It will be appreciated that, while the representation of FIG. 13 relates to patients who are or who are not responsive to endobronchial valve therapy, the same technique may be used for any of a variety of LVR therapies seeking atelectasis.

In another example, it can be seen that there is low fissure integrity likelihood at to a second portion in the RUL in non-responders, while there is high fissure integrity likelihood at the second portion in the RUL in responders. Accordingly, it may be that the second portion of the RUL is an important fissure portion for efficacy of endobronchial valve therapy. In general, voxel-by-voxel probabilistic maps of fissure integrity likelihood such as that shown in FIG. 13 provide a visual representation of which fissure portions may be important for efficacy of certain treatments.

With further reference to FIG. 13, global analysis of the RUL scan of a patient in the group of responders may yield a relatively low overall fissure integrity score. That is, as shown in the upper right image of FIG. 13, a patient in the group of responders may show an incomplete fissure at the third portion of the RUL. As a result, a global fissure integrity measurement of the RUL may be low enough to suggest that LVR therapy will be ineffective based on the global analysis. However, FIG. 13 suggests that local fissure incompleteness at the third portion of the RUL may not prohibit a patient from responding to a treatment. Accordingly, voxel-by-voxel analysis of fissure integrity likelihood data of responders and non-responders may improve the ability to predict the likelihood of therapy efficacy when compared to global fissure integrity measurements.

In some instances, LVR treatment procedures may be ineffective for reasons other than fissure incompleteness. For example, one or more valves placed in one or more portions of a patient's lungs may be inappropriately sized for the position in which they are placed. Additionally or alternatively, one or more valves may be misplaced or misaligned within the lungs. Accordingly, one or more valves placed within the patient may not properly provide the outcome intended by the LVR procedure. Ineffectiveness of such therapy may not be due patient selection, but rather may be caused by procedural errors. As a result, scans of patients who received therapy including procedural errors may be indexed into a non-responder atlas, even though the patient's fissure integrity may be high and indicative of a potential responder. This may skew statistical analysis of the effect of fissure integrity on therapy efficacy such as the analysis described above. In addition to treatment procedural issues described above, other factors may affect fissure metrics, such as local motion of proximate the lungs (e.g., of the heart or diaphragm). Such motion may affect the appearance of the fissure in scan data, and may make it appear incomplete in some regions, falsely impacting the fissure completeness score.

In various embodiments, data can be weighted to account for factors that may affect the reliability of the fissure metric analysis. That is, when generating an atlas or compiling fissure data from an atlas, data contributions from certain scans or voxels may be weighted based on a confidence in their dependence on fissure metrics. For instance, if a scan in a non-responder atlas is from a patient having a misaligned valve from an LVR procedure, the fissure data from that patient may not be reflected in the determination of the fissure integrity likelihood for non-responders. That is, in determining the fissure integrity likelihood for a given voxel among non-responders, data from the patient with the misaligned valve may be weighted less than other data sets. The weighting can be done on the data set as a whole, or on a subset of voxels affected by the misalignment. In general, a confidence weight may be included in statistical analysis of the fissure data in order to compensate for possible unrelated contributors to therapy response or other fissure data. The confidence weight may be applied on a scan-by-scan basis, a voxel-by-voxel basis, or in other various volumetric subdivisions, such as lobes, sub-lobes, or other definable sets of voxels. In some examples, confidence weights can be applied to the data used in the generation of fissure integrity likelihood maps such as shown in FIG. 13. In general, a weighting mechanism or other integration of prior information such as valve placement issue can be interpreted in a statistical framework and seen as a way to improve the classification accuracy. In various embodiments, other prior information known to have an impact on fissure completeness could be similarly considered to improve the maximum a posteriori solution.

Figure 14:
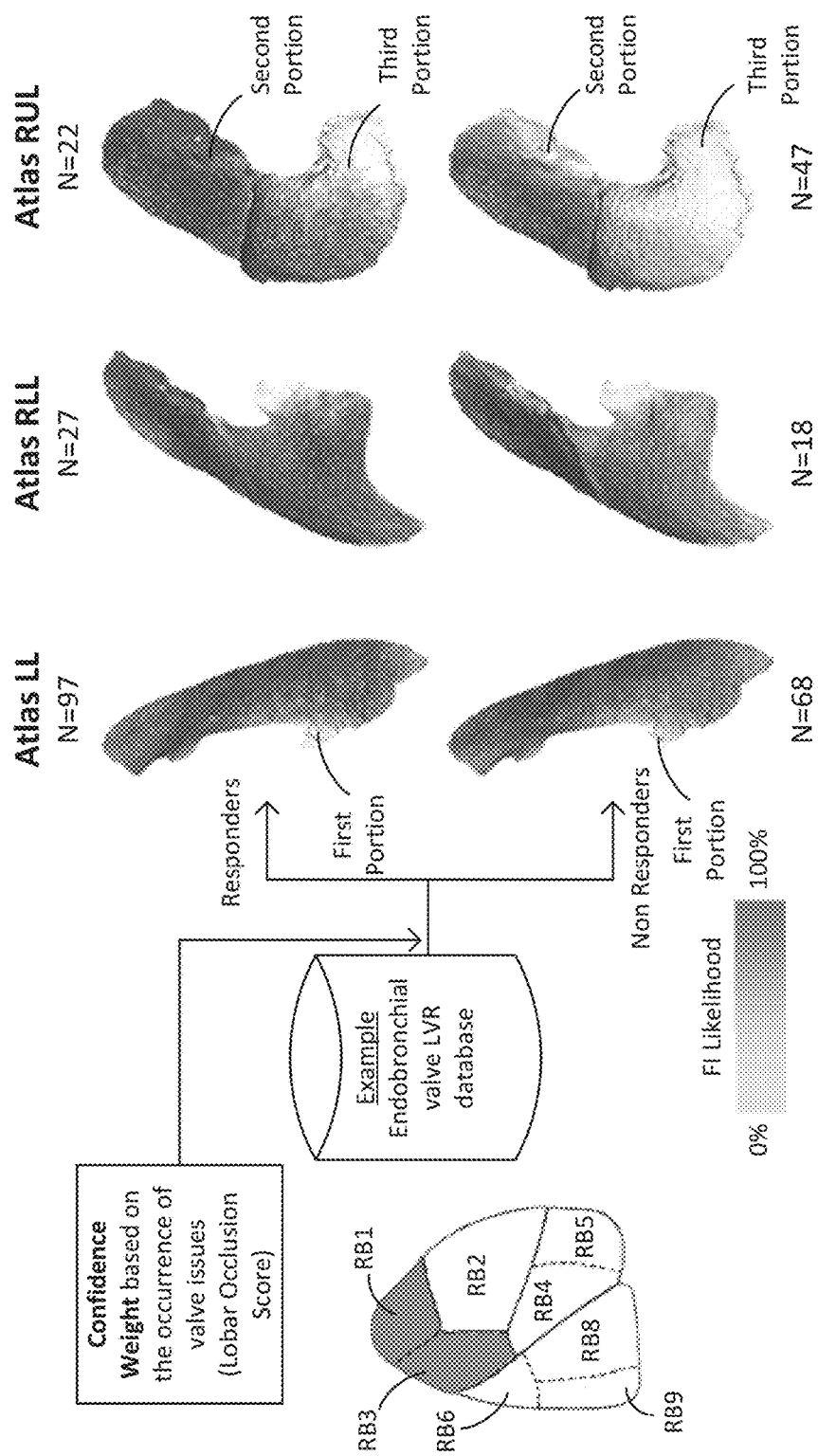
FIG. 14 is a visual representation of the relationship between the fissure integrity likelihood and response to a treatment including confidence weights based on valve issues.

FIG. 14 is a visual representation of the relationship between the fissure integrity likelihood and response to a treatment including confidence weights based on valve issues. As with FIG. 13, the upper section of FIG. 14 includes atlases of the left lung (LL, either left lower or left upper lobe), the right lower lobe (RLL), and the right upper lobe (RUL) for responders to endobronchial valve therapy. Each atlas is statistically analyzed to determine the fissure integrity likelihood among the atlas at each voxel. The lower section of FIG. 14 shows similar data for non-responders. However, FIG. 14 includes a confidence weight associated with entries in the atlases to be combined and compared. Weighting can be performed on a voxel-by-voxel basis, or may be performed for sets of multiple voxels, such as lobes or sub-lobes.

For instance, in the illustrative example, information about lung segments associated with valve positioning issues (highlighted RB1 and RB3 segments in the treated RUL) can be used to adjust the fissure integrity atlas. That is, due to known information regarding the lung segments associated with the valve positioning issues, the data contributing to the fissure integrity likelihood scores at voxels associated with those segments can be weighted accordingly. In general, weighting can be performed according to any voxel selection routine, such as voxels corresponding to lobes, sub-lobes, or arbitrarily-shaped sub-segments of the fissures (e.g., cylindrical, cubic, etc.).

In an exemplary embodiment, a Lobar Occlusion Score (LOS) is computed a posteriori for each patient and individual treated lobe to determine the segments for which valves have been improperly positioned. In some such embodiments, the LOS score is simply the percentage of the volume of affected sub-lobes relative to the overall lobar volume. The LOS can then be used to weight the contribution of each sub-lobe to the fissure atlas, such as by way of the confidence weight of FIG. 14. In some examples, this correction is particularly important for non-responders, since improperly positioned valves may be more likely to falsely indicate non-response than a positive response.

Figure 15:
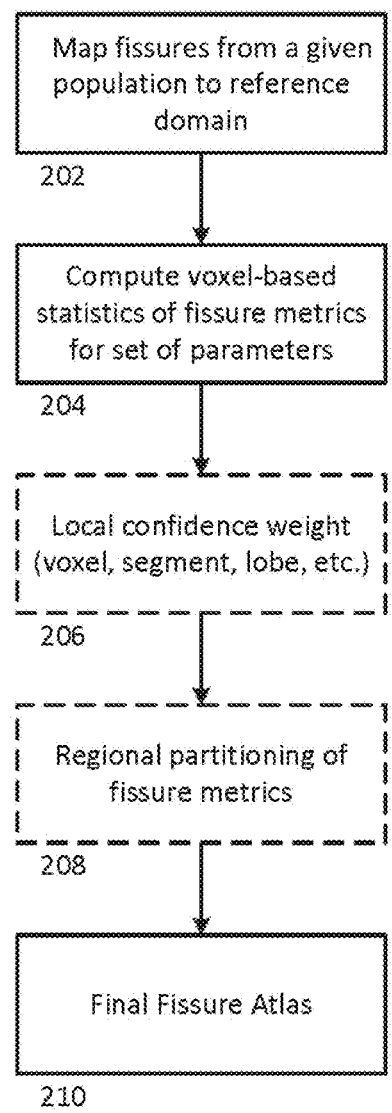
FIG. 15 is a process flow diagram illustrating an exemplary method of generating a final fissure atlas.

Various processes described above can be performed in order to generate a final fissure atlas. FIG. 15 is a process flow diagram illustrating an exemplary method of generating a final fissure atlas. Fissures from a given population are mapped to a reference domain (202). As described above, the reference domain can include fissure data from a single patient or a set of patients, for example. Once the fissure surfaces are mapped to a singled reference domain, voxel-based statistics of fissure metrics can be computed for a set of parameters (204). For example, a fissure integrity likelihood score can be determined for each voxel within the population of fissure surfaces. In some examples, various metrics can be computed according to confidence weights as described above (206). Additionally or alternatively, voxels can be partitioned into regions of interest (208). Regions of interest can be defined by lobes, sub-lobes, or other defining boundaries, such as customized volumes of a defined size and shape. In some examples, regions may be defined based on determined fissure metrics. Voxel-based statistics among a population, which may be weighted per step 206, can be combined into a final fissure atlas (210). The final fissure atlas may include regional partitions as defined in step 208.

In some embodiments, comparison data can be generated and displayed for comparing statistical data between groups in an atlas or between atlases. For instance, regarding FIGS. 13 and 14, comparisons between atlases of responders (e.g., the upper row of atlases) and non-responders (e.g., the lower row of atlases) to a particular LVR therapy can be performed for determining areas with significant differences between populations. These areas may have a higher correlation to treatment efficacy than areas without significant differences between populations when predicting whether or not a patient will respond to a treatment.

Figure 16:
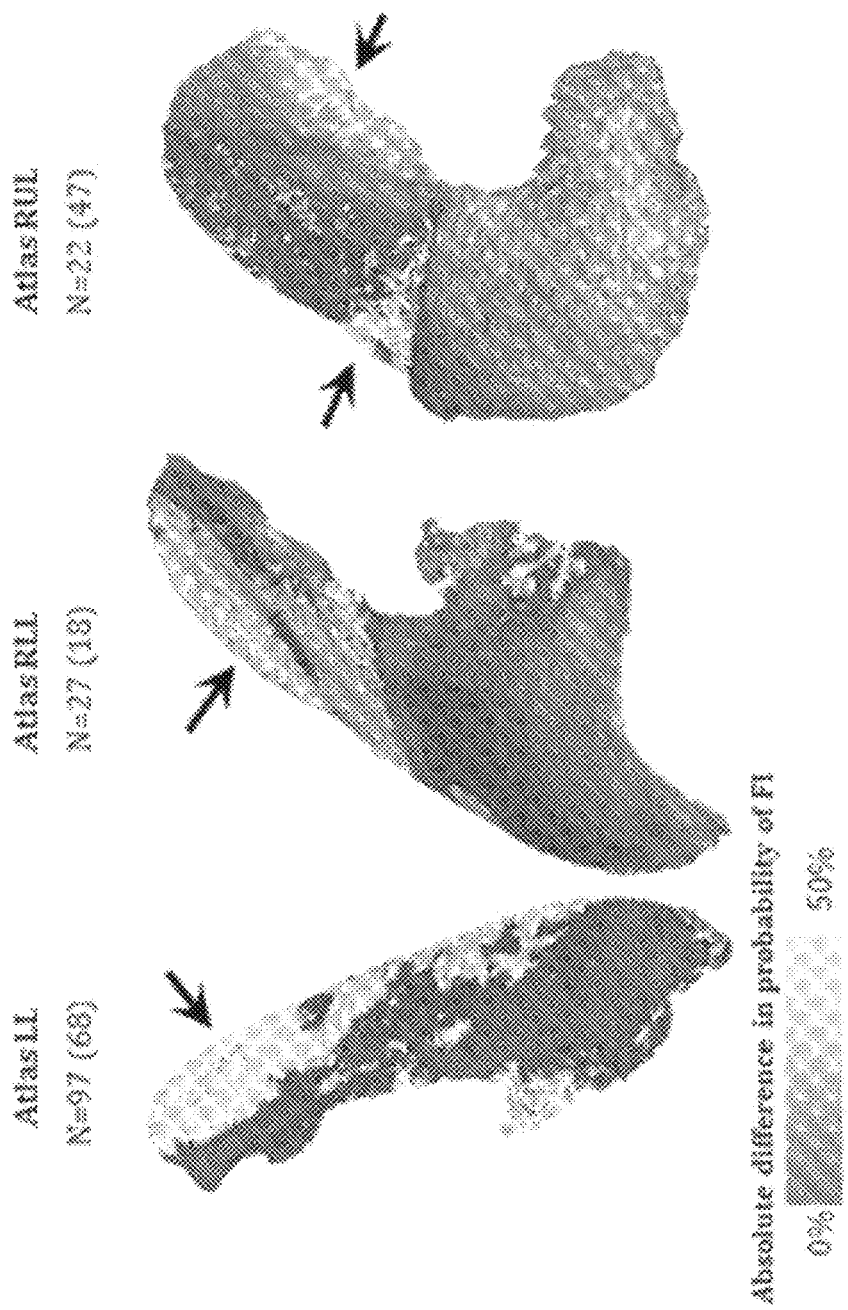
FIG. 16 is an illustration highlighting the absolute differences between the fissure probability maps of LVR responders and LVR non-responders from FIG. 13.
Figure 17:
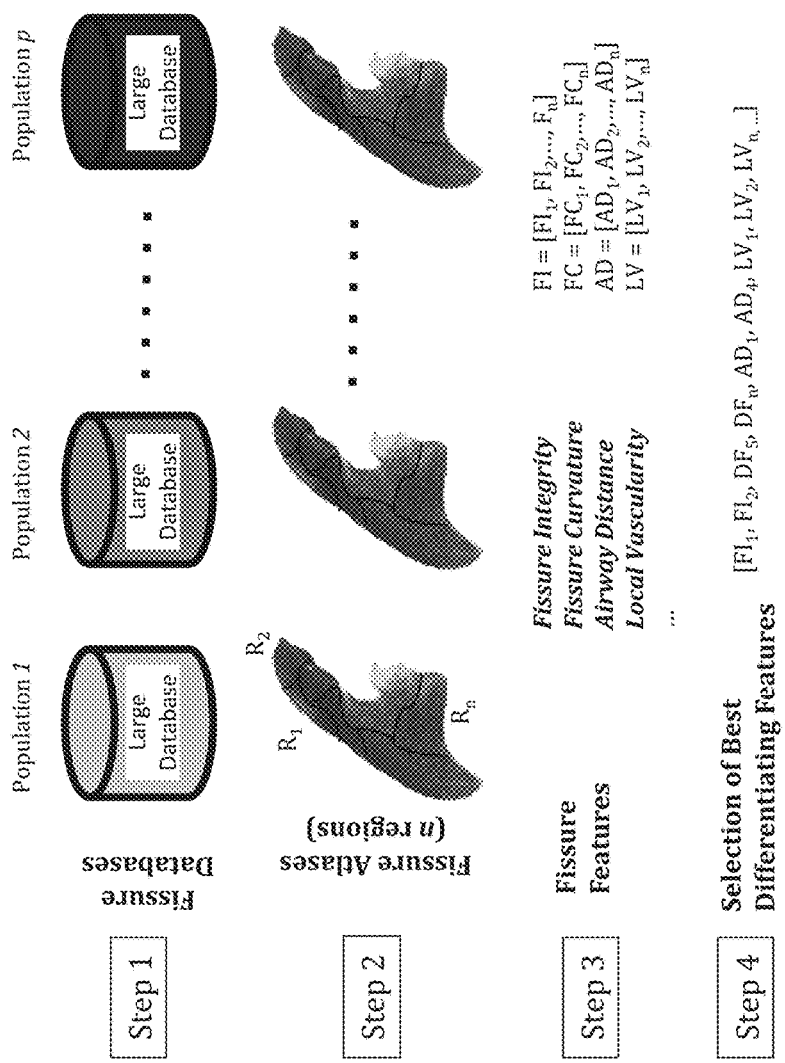
FIG. 17 is a diagram illustrating an exemplary process for determining differentiating features among populations.

FIG. 16 is an illustration highlighting the absolute differences between the fissure probability maps of LVR responders and LVR non-responders from FIG. 13. As shown in FIG. 16, the lighter areas indicate differences in fissure integrity likelihood nearing 50%, whereas darker areas indicate minimal differences in fissure integrity likelihood between responders and non-responders. Thus, since the darker areas show little difference between fissure integrity likelihood between responders and non-responders, the corresponding fissure portions may not be crucial to determining the likelihood of responding to LVR therapy. While the absolute difference between integrity likelihood in responders and non-responders is illustrated in FIG. 16, it will be appreciated that other mechanisms may be used to combine or compare sets of data. In general, one or more such comparisons and combinations of data may be selected in order to determine distinguishable characteristics between responders and non-responders FIG. 17 is a diagram illustrating an exemplary process for determining differentiating features among populations. As shown, in Step 1, a series of fissure databases representative of different populations $P_1, P_2 \ldots P_p$ are defined. Exemplary populations can include, for instance, responders or non-responders to a LVR therapy. In general, any number of populations may be defined. Next, in Step 2, each entry in each of the databases is processed into a fissure atlas associated with each population. Processing each entry in the database can include, for instance, mapping each entry in the database to a reference domain. In some example, creating the fissure atlas includes a combination of each of the entries from the database being entered into the atlas, such as the various weighted combining processes described above. Processing can further include identifying various regions of interest within the reference domain for comparative analysis. For instance, the reference domain may be partitioned into lobes, sub-lobes, or custom-defined volumetric regions. This is illustrated in FIG. 17 by the division of the reference domain (and similarly, each entry from the database that was mapped to the reference domain) into regions $R_1, R_2 \ldots R_n$. In some embodiments, the generation of fissure atlases in Step 2 may be performed in a similar manner to the method of FIG. 15.

Once the fissure atlases have been defined in Step 2, fissure features can be determined in Step 3 and computed in the reference domain. In various embodiments, fissure features may be associated with each region defined by the atlas. For example, fissure features associated with each region can include: a fissure integrity score, the deviation of the fissure surface from the mean model, distance between a fissure surface regional area and other lung structures including but not limited to a series of airway branch or a specific branch, vascular trees (arteries, veins), CT density on fissure surfaces, and other quantitative measurements projected on fissure surfaces, and the like. Such data can be determined for each region in each fissure atlas. As shown, data can be stored according to regions, for instance, in a vector.

According to Step 4, fissure features may be selected based on their relative predictive value to procedural outcome or disease contribution. In the particular example of FIG. 17, differentiating features include the fissure integrity of regions 1 and 2, the deformation fields of regions 5 and n, airway distances of regions 1 and 4, and the local vascularity of regions 1, 2, and n. The selected differentiating features may vary depending on the different populations being compared. In general, differentiating features may be determined by a variety of methods, such as comparisons or other statistical analysis of data in each atlas (e.g., each population). Various features may be directly compared to other atlases, or may be used to modify the comparison. For instance, in some examples, the airway distance feature may be used to weight the fissure integrity score from its respective region if the airway distance is determined to affect the importance of the fissure integrity of that region. Additionally or alternatively, since in some examples it may be easier to analyze vascularity of a patient than airway structure, and that vascularity may closely mirror airway structure, the vascularity data may work to enhance the airway distance data. In some embodiments, the selection of best differentiating features can be performed using known feature selection methods or by assessing the predictive ability of features using various classification schemes, as will be described below.

The selected best differentiating features may be used to train a classifier, as shown in Step 5. A trained classifier may help predict in which population a yet unclassified data set belongs. For example, if populations are determined by whether or not a patient is a responder to an LVR procedure, classification of a scan for a new patient may comprise predicting whether or not the patient is likely to be a responder to the LVR procedure. Classification can be performed according to a variety of methods. For example, for an unclassified set of data, the set of data can be mapped to the reference domain and its associated fissure features can be determined. The differentiating features of the unclassified data can then be analyzed, and the data can be classified according to its differentiating features. The classified data can be added to an appropriate database.

In some embodiments, a variety of the steps of FIG. 17 may be performed according to a variety of classification and selection schemes. For instance, in some embodiments, Feature selection approaches aim to select a small subset of features. For the classification problem, feature selection aims to select subset of highly discriminant features such as the features highlighted in step 4 of FIG. 17. In other words, it selects features that are capable of discriminating patient data that belong to different classes (responders vs. non-responders, disease vs. healthy, etc.). Classification in step 5 of FIG. 17 consist in identifying to which of a set of categories (sub-populations) a new patient data belongs, on the basis of a training set of data containing patient data (or instances) whose class membership is known. Classification is performed using discriminant features identified in step 4. For the purpose of this invention, may combinations of feature selection and classification methods can be used and explored. We refer to state-of-the-art literature in machine learning (ex. M Sonka, V Hlavac, R Boyle. Image Processing, Analysis, and Machine Vision. Fourth Edition. 2014.)

Figure 18:
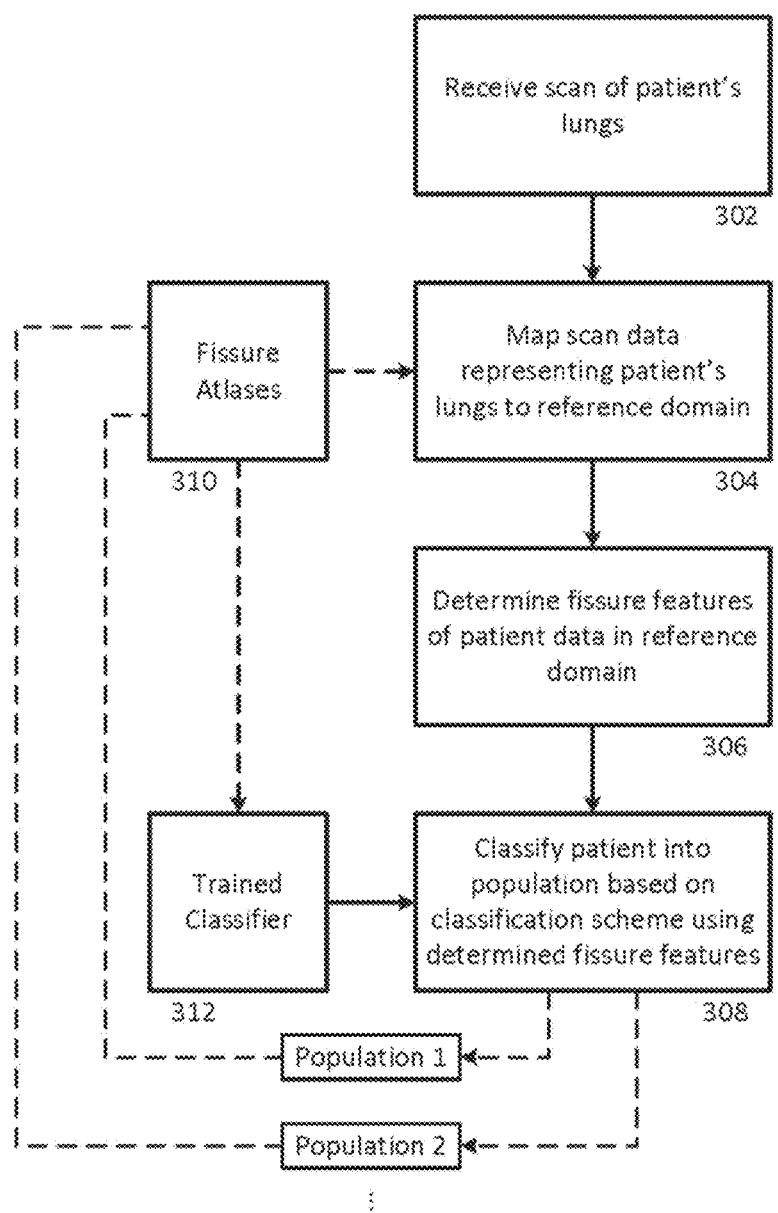
FIG. 18 is a process flow diagram demonstrating the classification of a patient according to some embodiments.

As previously described, the method described in FIG. 17 may be used to identify patients likely to respond to a treatment or directly associated with a disease state based solely on scan data, and prior to the procedure to be performed. FIG. 18 is a process flow diagram demonstrating the classification of a patient. First, a scan of the patient's lungs is received (302). The scan data can be mapped to a reference domain (304). Mapping to the reference domain may allow for consistent analysis with a database of classification data. In some examples, the reference domain may be defined by a fissure atlas 310 containing a series of patient scans, each represented in the reference domain. Once mapped to the reference domain, a variety of fissure related features of the patient data can be determined (306). Finally, based on the determined fissure related features of the patient data, the patient may be classified (308) using a classifier 312 trained on the fissure atlases 310.

The classifier 312 may identify a plurality of populations (e.g., responders, non-responders) into which to group patients as described with regard to FIG. 17. In some such examples, the populations may each be identified according to a unique fissure atlas in fissure atlases 310. Accordingly, the process described in FIG. 18 may be used as a predictive method for determining, for example, whether or not a patient is likely to respond to a LVR or other treatment therapy based on scan results. As a result, therapy may be selectively provided to those likely to respond to the therapy. In another application, a similar procedure may be used to determine which course of therapy is most likely to cause a patient to respond, and therefore may be used in a treatment program selection process.

EXPERIMENTAL

The following experimental description illustrates results of predictive classification schemes. Treatments are broken down into left upper/lower lobe treatment, right upper lobe treatment, and right lower lobe treatment. Given a database of patient data and knowledge of whether or not the patient responded to the given therapy, the sensitivities and specificities of predictive models are given for a variety of therapies. In addition, such metrics are recorded for various regional divisions for analyzing fissure integrities. For instance, classification was performed based on lobar, sub-lobar, and regional (sub-segmental) fissure integrity analysis.

BACKGROUND: Fissure integrity (FI) as a global measurement of lobar collateral ventilation has been shown to correlate to response of valve-based lung volume reduction (L VR) therapy.

OBJECTIVES: To determine if regional FI can further influence outcome by providing a more localized predictor.

METHODS: Automated regional FI analysis of 253 subjects treated with valves was analyzed in Apollo (VIDA Diagnostics, IA). Individual fissures separating the treated lobe from its ipsilateral lobe were spatially matched to the corresponding ones in a reference patient, allowing voxel-based comparisons of fissure properties between responders (n=141) and non-responders (n=112). Regional FIs were derived based on sub-lobar contact areas or further divided smaller sub-segmental regions on fissure surface. Predictions of L VR outcome using lobar FI, sub-lobar FI and sub-segmental FI were obtained using a Naive Bayes classifier with 10-fold cross-validation to avoid over-optimistic results.

RESULTS: Lobar distribution of LVR treatment for responders/non-responders is: RUL (36/21), RLL (19/14), LUL/LLL (101/62). The sensitivity and specificity values are listed in Table 1 below. Both methods of local FIs yield better classification results than the global FI.

CONCLUSION: The results suggest regional FI biomarkers could expand patient selection for valves and lead to more targeted, personalized treatments for emphysema patients including other LVR techniques.

TABLE 1

| LVR outcome prediction using lobar FI, sub-lobar FI, and sub-segmental FI | | | | | | | | |
|---|---|---|---|---|---|---|---|---|
| Left upper/lower lobe treatment (N = 163) | | | Right upper lobe treatment (N = 57) | | | Right lower lobe treatment (N = 33) | | |
| Lobar FI | Sub-Lobar FI | Sub-seg FI | Lobar FI | Sub-Lobar FI | Sub-seg FI | Lobar FI | Sub-Lobar FI | Sub-seg FI |
| Sensitivity (%) 96 | 98 | 97 | 90 | 95 | 95 | 58 | 95 | 100 |
| Specificity (%) 12 | 21 | 26 | 9 | 92 | 78 | 57 | 50 | 79 |

As shown, when compared to a global, lobar FI metric, sub-lobar and sub-segmental fissure integrity analysis often results in improved sensitivity (true positives) and specificity (true negative) when predicting the efficacy of an LVR treatment.

In the foregoing detailed description, the invention has been described with reference to specific embodiments. However, it may be appreciated that various modifications and changes can be made without departing from the scope of the invention.

The invention claimed is:

1. A method for analyzing a patient based on a volumetric pulmonary scan comprising:
    receiving a first volumetric pulmonary scan representative of the patient's pulmonary structure;
    mapping the first volumetric pulmonary scan to a reference domain;
    determining one or more fissure features associated with a plurality of regions in the reference domain and within the first volumetric pulmonary scan;
    comparing, in each of the plurality of regions, the determined one or more fissure features to a plurality of fissure atlases, each atlas comprising statistical data associated with the one or more fissure features for a population based on regional analysis of volumetric pulmonary scans of that population;
    classifying the patient into one or more of the populations based on the comparison of the determined one or more fissure features.

2. The method of claim 1, further comprising:
    after the classifying the patient into the one or more of the populations, adding the mapped first volumetric pulmonary scan to the fissure atlas associated with the one or more of the populations; and
    updating the statistical data in the fissure atlas to include the first volumetric pulmonary scan.

3. The method of claim 2, wherein updating the statistical data in the fissure atlas to include the first volumetric pulmonary scan data comprises weighting the contribution from the first volumetric pulmonary scan data in the fissure atlas at each of a plurality of regions.

4. The method of claim 1, wherein the one or more of the populations comprises responders to a particular therapy and non-responders to the particular therapy.

5. The method of claim 1, wherein the one or more of the populations comprises patients with collateral ventilation and patients without collateral ventilation.

6. The method of claim 1, wherein the first volumetric pulmonary scan comprises a CT scan, an MRI scan, or a PET scan.

7. The method of claim 1, further comprising:
    identifying, for a given fissure feature, distinguishing regions in the volumetric pulmonary scans wherein the given fissure feature is substantially different among the one or more of the populations; and wherein
    comparing the determined one or more fissure features to a plurality of fissure atlases comprises, for the given fissure feature, comparing the given fissure feature in the first volumetric pulmonary scan data to the plurality of fissure atlases in the identified distinguishing regions.

8. The method of claim 7, wherein a set of distinguishing regions are identified corresponding to a pair of fissure atlases and a single fissure feature; and wherein
    for a given fissure feature and pair of the one or more of the populations, the distinguishing regions comprise regions in which the difference between the fissure feature in the pair of fissure atlases is considered significant.

9. The method of claim 8, further comprising:
    in each of a plurality of regions, statistically analyzing the fissure feature in a first fissure atlas and the fissure feature in a second fissure atlas and determining the regions in which the difference between the fissure feature in the two atlases is significant in order to determine distinguishing regions corresponding to the first and second fissure atlases and the first fissure feature.

10. The method of claim 1, wherein the one or more fissure features comprises a feature selected from the group consisting of: fissure integrity, fissure curvature, airway related measurements, deformation field, local vascularity related measurements, and local parenchymal related features.

11. A system for assessing a volumetric pulmonary scan of a patient comprising:
    a database comprising a plurality of fissure atlases, each fissure atlas comprising statistical data regarding one or more fissure features in a plurality of volumetric pulmonary regions for a population; and a processor configured to:
    statistically analyze the one or more fissure features in the plurality of volumetric pulmonary regions to determine, for each fissure feature, one or more distinguishing regions;
    receive a first set of volumetric pulmonary scan data representative of the volumetric structure of a patient's lungs;
    determine the one or more fissure features in the first set of volumetric pulmonary scan data at a plurality of regions;
    compare the determined one or more fissure features to the plurality of fissure atlases in the database; and
    classify the first set of volumetric pulmonary scan data into one or more of the populations based on the comparison.

12. The system of claim 11, wherein the processor is further configured to:
    after the classifying the first set of volumetric pulmonary scan data into the one or more of the populations, add the first volumetric pulmonary scan data to the fissure atlas associated with the one or more of the populations; and
    update the statistical data in the fissure atlas to include the first volumetric pulmonary scan data.

13. The system of claim 11, wherein the processor is further configured to:
    analyze the one or more fissure features in each of a plurality of volumetric pulmonary regions in each of the plurality of fissure atlases;
    determine, for each fissure feature, one or more distinguishing regions in the plurality of regions, the one or more distinguishing regions being regions in which the fissure feature differs significantly between at least two fissure atlases; and
    associate the determined distinguishing regions with the corresponding fissure feature and fissure atlases.

14. The system of claim 13, wherein classifying the first set of volumetric pulmonary scan data into the one or more of the populations based on the comparison comprises comparing determined fissure features from the first set of volumetric pulmonary scan data to corresponding fissure atlases in the determined distinguishing regions.

15. The system of claim 11, wherein the statistical data in each of the fissure atlases is associated with regions in a reference domain, and wherein the processor is further configured to map the first set of volumetric pulmonary scan data to the reference domain.

16. The system of claim 11, wherein the processor further configured to identify regions in the reference domain, and wherein the identified regions comprise lobes, sub-lobes, and/or custom-defined regions.

17. A method comprising:
    acquiring a first plurality of three-dimensional pulmonary models, each of the models being representative of the pulmonary structure of a patient belonging to a first population;
    registering each of the three-dimensional models in the first plurality of three-dimensional models to a reference domain to create a first atlas;
    statistically analyzing the first plurality of registered three-dimensional models in the first atlas to determine a first fissure feature at each of a plurality of regions in the first atlas;
    acquiring a second plurality of three-dimensional pulmonary models, each of the models being representative of the pulmonary structure of a patient belonging to a second population, the second population being different from the first;
    registering each of the three-dimensional models in the second plurality of three-dimensional models to the reference domain to create a second atlas;
    statistically analyzing the second plurality of registered three-dimensional models in the second atlas to determine the first fissure feature at each of a plurality of regions in the second atlas;
    for each of a plurality of regions in the first and second atlases, comparing the first fissure feature of the first atlas to the first fissure feature of the second atlas to determine regions in which the first fissure feature differs significantly between the first and second populations and considering such regions to be distinguishing regions associated with the first population, the second population, and the first fissure feature;
    receiving a diagnostic three-dimensional pulmonary model of a first patient's lungs;
    registering the received diagnostic three-dimensional pulmonary model to the reference domain;
    analyzing the first fissure feature in the distinguishing regions in the diagnostic three-dimensional pulmonary model; and
    predicting if the first patient is in the first population or the second population based on the analyzed first fissure feature in the distinguishing regions in the diagnostic three-dimensional pulmonary model.

18. The method of claim 17, wherein:
    the first population comprises patients who responded positively to a particular therapy;
    the second population comprises patients who did not respond positively to the particular therapy; and
    the comparing the first fissure feature of the first atlas to the first fissure feature of the second atlas for each of the plurality of regions comprises determining a correlation between the first fissure feature in each region and the effectiveness of the particular therapy.

19. The method of claim 18, wherein determining a correlation between the first fissure feature in each region and the effectiveness of the particular therapy comprises determining in which of the plurality of regions the difference in the first fissure feature between the first population and the second population is greatest.

20. The method of claim 18, wherein the first fissure feature comprises a feature selected from the group consisting of: fissure integrity, fissure curvature, airway related measurements, deformation field, local vascularity related measurements, and local parenchymal related features.

21. The method of claim 17, further comprising:
    for each of a plurality of regions in the first and second atlases, comparing the each of a plurality of fissure features of the first atlas to a corresponding fissure feature of the second atlas to determine, for each fissure feature, regions in which that fissure feature is most different between the first and second populations and considering such regions to be distinguishing regions with associated with the first population, the second population, and that fissure feature.

22. The method of claim 17, wherein
    the first population comprises patients who display at least one diagnostic symptom;
    the second population comprises patients who do not display the at least one diagnostic symptom; and
    the comparing the first fissure feature of the first atlas to the first fissure feature of the second atlas for each of the plurality of regions comprises determining a correlation between the first fissure feature in each region and the likelihood of a patient displaying the at least one diagnostic symptom.

23. The method of claim 22, wherein the at least one diagnostic symptom comprises collateral ventilation.

24. The method of claim 23, wherein the first fissure feature is based on an airway distance.

* * * * *